US007790454B2

(12) United States Patent
Bullerdiek

(10) Patent No.: US 7,790,454 B2
(45) Date of Patent: Sep. 7, 2010

(54) METHOD FOR TISSUE REGENERATION

(76) Inventor: Jorn Bullerdiek, Weibdornpfad 14, D-28355 Bremen (DE)

( * ) Notice: Subject to any disclaimer, the term of this patent is extended or adjusted under 35 U.S.C. 154(b) by 0 days.

(21) Appl. No.: 11/024,522

(22) Filed: Dec. 29, 2004

(65) Prior Publication Data
US 2005/0186210 A1 Aug. 25, 2005

Related U.S. Application Data

(63) Continuation of application No. 09/951,107, filed on Sep. 10, 2001, now abandoned, which is a continuation of application No. 09/105,542, filed on Jun. 26, 1998, now Pat. No. 6,323,329, which is a continuation-in-part of application No. 09/102,321, filed on Jun. 22, 1998, now abandoned, which is a continuation of application No. PCT/DE96/02494, filed on Dec. 20, 1996.

(30) Foreign Application Priority Data
Dec. 21, 1995 (DE) ................................ 195 48 122

(51) Int. Cl.
C12N 5/00 (2006.01)
(52) U.S. Cl. ....................................................... 435/375
(58) Field of Classification Search ........................ None
See application file for complete search history.

(56) References Cited

FOREIGN PATENT DOCUMENTS

EP 0 727 487 A1 7/1995

OTHER PUBLICATIONS

Asher, et al. "Disruption of the Architectural Factor HMGI-C: DNA-Binding at AT Hook Motifs F used in Lipomas to Distinct Transcriptional Regulatory Domains," Cell, vol. 82, pp. 57-65, Jul. 14, 1995.
Chau, et al. "The Gene for the Human Architectural Transcription Factor HMGI-C Consists of Five Exons Each Coding for a Distinct Functional Element," Nucleic Acids Research, vol. 23, No. 21, pp. 4282-4286, 1995.
Kazmierczak, et al. "Description of a Novel Fusion Transcript Between HMGI-C, a Gene Encoding for a Member of the High Mobility Group Proteins, and the Mitochondrial Aldehyde Dehydrogenase Gene," Cancer Research, vol. 55, pp. 6038-6039, Dec. 15, 1995.
Manfioletti, et al. "Isolation and Characterization of the Gene Coding for Murine High-Mobility-Group Protein HMGI-C," Gene, vol. 167, pp. 249-253, 1995.
Patel, et al., "Expression and cDNA Cloning of Human HMGI-C Phosphoprotein," Biochemical and Biophysical Research Communications, vol. 201, No. 1, pp. 83-70, May 30, 1994.
Schoenmakers, et al., "Recurrent Rearrangements in the High Mobility Group Protein Gene, HMGI-C, in Benign Mesenchymal Tumours," Nature Genetics, vol. 10, pp. 438-444, 1995.
Zhou, et al., "Mutation Responsible for the Mouse Pygmy Phenotype in the Developmentally Regulated Factor HMGI-C," Nature, vol. 378, pp. 771-774, Aug. 31, 1995.
Holden, et al. "Plasticity: Time for a Reappraisal?," Science, vol. 296, pp. 2126-2129, Jun. 21, 2002.
Feldman, et al., "Anti-TNFα Therapy is Useful in Rheumatoid Arthritis and Crohn's Disease: Analysis of the Mechanism of Action Predicts Utility in Other Diseases," Transplantation Proceedings, vol. 30, pp. 4126-4127, 1998.
Anisimov, S. V., K. V. Tarasov, et al. (2002). "SAGE identification of differentiation responsive genes in P19 embryonic cells induced to form cardiomyocytes in vitro." Mech Dev 117: 25-74.
Arlotta, P., A. K. Tai, et al. (2000). "Transgenic mice expressing a truncated form of the high mobility group I-C protein develop adiposity and an abnormally high prevalence of lipomas." J Biol Chem 275: 14394-400.
Battista, S., F. Pentimalli, et al. (2003). "Loss of Hmga1 gene function affects embryonic stem cell lympho-hematopoietic differentiation." FASEB J 17: 1496-8.
Caron, L., F. Bost, et al. (2005). "A new role for the oncogenic high-mobility group A2 transcription factor in myogenesis of embryonic stem cells." Oncogene 24: 6281-91.
Chin, M. T., A. Pellacani, et al. (1999). "Induction of high mobility group I architectural transcription factors in proliferating vascular smooth muscle in vivo and in vitro." J Mol Cell Cardiol 31: 2199-205.
D'Armiento, J., K. Imai, et al. (2007). "Identification of the benign mesenchymal tumor gene HMGA2 in lymphangiomyomatosis." Cancer Res 67: 1902-9.
Hirning-Folz, U., M. Wilda, et al. (1998). "The expression pattern of the Hmgic gene during development." Genes Chromosomes Cancer 23: 350-7.
Inoue, N., T. Izui-Sarumaru, et al. (2006). "Molecular basis of clonal expansion of hematopoiesis in two patients with paroxysmal nocturnal hemoglobinuria (PNH)." Blood 108:4232-6.
Kubo, T., Y. Matsui, et al. (2006). "Overexpression of HMGA2-LPP fusion transcripts promotes expression of the alpha 2 type XI collagen gene." Biochem Biophys Res Commun 340: 476-81.
Li, O., J. Li, et al. (2007). "DNA architectural factor and proto-oncogene HMGA2 regulates key developmental genes in pluripotent human embryonic stem cells." FEBS Lett 581: 3533-7.
Ligon, A. H., S. D. Moore, et al. (2005). "Constitutional rearrangement of the architectural factor HMGA2: A novel human phenotype including overgrowth and lipomas." Am J Hum Genet 76: 340-8.

(Continued)

Primary Examiner—Michail A Belyavskyi
(74) Attorney, Agent, or Firm—Knobbe Martens Olson & Bear LLP

(57) ABSTRACT

The invention relates to DNA-sequences, their use and the use of DNA-sequences of the MAG gene or genes encoding the high mobility group proteins, agents for the treatment of various diseases including tumors, influencing the development of the vascular system, as well as for contraception and tissue regeneration, and appropriate kits and processes. The sequences, agents, uses, kits and processes enable the specific influencing of molecular mechanisms that jointly form the basis for various diseases, the development of the vascular system, the contraception and the regeneration of tissue. Thus, the disadvantages associated with other agents or processes are decreased.

1 Claim, 1 Drawing Sheet

OTHER PUBLICATIONS

Lord-Grignon, J., M. Abdouh, et al. (2006). "Identification of genes expressed in retinal progenitor/stem cell colonies isolated from the ocular ciliary body of adult mice." Gene Expr Patterns 6: 992-9.

Matsui, Y., T. Hasegawa, et al. (2006). "Intrapatellar tendon lipoma with chondro-osseous differentiation: detection of HMGA2-LPP fusion gene transcript." J Clin Pathol 59: 434-6.

Melillo, R. M., G. M. Pierantoni, et al. (2001). "Critical role of the HMGI(Y) proteins in adipocytic cell growth and differentiation." Mol Cell Biol 21: 2485-95.

Monzen, K., Y. Ito, et al. (2008). "A crucial role of a high mobility group protein HMGA2 in cardiogenesis." Nat Cell Biol 10: 567-74.

Pierantoni, G. M., V. Agosti, et al. (2003). "High-mobility group A1 proteins are overexpressed in human leukaemias." Biochem J 372: 145-50.

Sanosaka, T., M. Namihira, et al. (2008). "Identification of genes that restrict astrocyte differentiation of midgestational neural precursor cells." Neuroscience. 2008 [Epub ahead of print].

Van Dorpe, J., P. Dal Cin, et al. (2002). "Translocation of the HMGI-C (HMGA2) gene in a benign mesenchymoma (chondrolipoangioma)." Virchows Arch 440: 485-90.

METHOD FOR TISSUE REGENERATION

RELATED APPLICATIONS

This application is a continuation of U.S. application Ser. No. 09/951,107, filed Sep. 10, 2001, now abandoned, which is a continuation of U.S. application Ser. No. 09/105,542, filed Jun. 26, 1998, now U.S. Pat. No. 6,323,329, which is a continuation-in-part of U.S. application Ser. No. 09/102,321, filed Jun. 22, 1998, now abandoned, which is a continuation of International Application PCT/DE96/02494, filed Dec. 20, 1996, which designates the United States and which claims priority to German application DE 195 48 122.4, filed Dec. 21, 1995.

FIELD OF THE INVENTION

The present invention relates to the fields of molecular biology and biotechnology. More specifically, the invention relates to compositions and methods based on DNA sequences of MAG genes or of genes of the high mobility group proteins and substances for: (1) treatment of diseases; (2) contraception; and (3) tissue generation. Corresponding kits and methods also are disclosed.

BACKGROUND OF THE INVENTION

When studying the molecular basis of aberrant cell growth that accompanies the growth of benign and malignant tumors, so-called MAG genes (multiple-tumor aberration growth genes) were identified as belonging to the group to which high mobility group protein (HMG genes) genes belong.

The genes of the high mobility group proteins, such as the HMGI-C gene located on the human chromosome 12 and the HMGI-Y gene on chromosome 6, which, among the known HMG genes, has the relative highest homologous degree compared to HMGI-C, usually have components that code for DNA-bonding protein parts and components that code for protein-bonding components.

Studies by Schoenmakers et al., (*Nature Genet* 10:436 (1995)) studies show that mutations of the HMGI-C gene are the most likely cause of the development of many benign human tumors, some groups of which are: uterus leiomyoma, lipoma, pleomorphic adenoma of the salivary gland, endometrium polyps, hamarto chondroma of the lung, aggressive angiomyxoma, and fibroadenoma of the mamma.

With the exception of the pleomorphic adenoma, all of the above tumors are of mesenchymal origin or contain mesenchymal components that are considered to be monoclonal. Today the pleomorphic adenoma is mostly considered to be an epithelial tumor, although its histogenesis still has not been completely determined and there are discussions concerning the participation of mesenchymalic cells in the development of tumors. Many of the tumors sometimes or even regularly show mesenchymalic metaplasia. Also striking is the appearance of myxoid cartilage in many of the tumors, which is characteristic of hamarto chondroma of the lung and the pleomorphic adenoma, for example. Ashar et al., (*Cell* 82:57 (1995)) confirmed the findings of Schoenmakers et al., (*Nature Genet* 10:436 (1995)) for the lipoma group.

DEFINITIONS

As used herein, it is to be understood that "HMGI genes" refers to a subfamily of high mobility group protein genes comprising HMGI-C and HMGI(Y). Furthermore, the respective translation products comprise HMGI-C encoded by the HMGI-C gene, and HMGI and HMGY both encoded by the HMGI(Y) gene.

SUMMARY OF THE INVENTION

A first aspect of the invention relates to an isolated polynucleotide having a sequence that includes a first sequence encoding each of exons 1, 2 and 3 of an HMGI or MAG gene, and a second sequence from a source other than an HMGI or MAG gene, wherein the second sequence is a human DNA sequence which is a sequence other than a sequence immediately upstream of exon 1 of the HMGI or MAG gene in a human genome. According to one embodiment of the invention, the second sequence of the isolated polynucleotide encodes a gene product which is encoded by one of SEQ ID NOS:1-19. According to another embodiment of the invention, the isolated polynucleotide has the sequence of one of SEQ ID NOS:1-19.

A second aspect of the invention relates to an isolated polypeptide having a sequence that includes a first sequence encoded by exons 1, 2 and 3 of an HMGI or MAG gene, and a second sequence encoded by a polynucleotide from a source other than an HMGI or MAG gene. The second polynucleotide is from a human, but has a sequence other than the sequence located immediately upstream of exon 1 of the HMGI or MAG gene in the human genome. According to one embodiment of the invention, the isolated polypeptide has a sequence encoded by one of SEQ ID NOS:1-9.

A third aspect of the invention relates to a method for treating tumors in a mammal. This method includes the steps of administering to the mammal an agent which blocks the activity or effect of a DNA selected from the group consisting of an HMGI gene, a MAG gene and a polynucleotide having a sequence which includes at least a first sequence encoding each of exons 1, 2 and 3 of an HMGI or MAG gene; and a second sequence which is from a source other than an HMGI or MAG gene. This second sequence is a human DNA sequence and is a sequence other than the sequence immediately upstream of exon 1 of the HMGI or MAG gene in the human genome. According to one embodiment the DNA has a sequence of one of SEQ ID NOS:1-19 or a sequence encoding the same amino acids encoded by SEQ ID NOS:1-19. Alternatively, agent inhibits the formation of transcripts of the HMGI or MAG genes. According to another embodiment, the agent decreases the half-life of the HMGI or MAG gene transcripts. According to yet another embodiment, the agent is selected from the group consisting of anti-sense nucleic acid molecules and ribozymes. According to still yet another embodiment, the agent is a translation product of the DNA molecule. According to a further embodiment, the administering step involves incorporating the agent into the tumor. This administering step can include introducing a vector to the tumor, where this vector includes the DNA or an RNA transcript thereof; and then expressing the DNA or RNA transcript to create translation products thereof which competitively inhibit binding of cellular HMGI/MAG gene translation products to the cellular genome. According to a different embodiment, the tumor is one which shows expression of a gene which is selected from the group consisting of HMGI genes, HMGI-C genes and HMGI-Y genes. In the alternative, the agent can be a nucleic acid having a sequence that includes at least one AT hook or at least one AT hook-like structure.

A fourth aspect of the invention relates to a method for diagnosing of tumors which includes the steps of: (1) administering to suspected tumor tissue a first polynucleotide which is complementary to a second polynucleotide that is selected from the group consisting of HMGI genes, MAG genes and nucleic acid molecules having sequences according to one of SEQ ID NOS.: 1-19; and (2) detecting significant complex formation between the first polynucleotide and the second polynucleotide when a tumor is present, but not when a tumor is absent. In this instance, the first polynucleotide additionally may include a marker or label.

A fifth aspect of the invention relates to a method for diagnosing tumors which includes the steps of: (1) administering to suspected tumor tissue a translation product of a polynucleotide selected from the group consisting of HMGI genes, MAG genes and nucleic acid molecules having sequences according to one of SEQ ID NOS.: 1-19; and then (2) detecting significant complex formation between the product and the polynucleotide when a tumor is present, but not when a tumor is absent. In a preferred embodiment of this method, the translation product includes a marker or label.

A sixth aspect of the invention relates to a method for diagnosing of tumors that involves the steps of: (1) administering to suspected tumor tissue an antibody to a translation product of a polynucleotide selected from the group consisting of HMGI genes, MAG genes and nucleic acid molecules having sequences according to one of SEQ ID NOS.: 1-19; and then (2) detecting significant complex formation between the antibodies and the translation products when a tumor is present, but not when a tumor is absent. In one embodiment of the invented method the antibody is selected from the group consisting of polyclonal antibodies, monoclonal antibodies and fragments and derivatives thereof. In a different embodiment the antibody includes a marker or label.

A seventh aspect of the invention relates to a method for diagnosis of endometriosis which involves: (1) administering a first polynucleotide to suspected ectopic endometrial tissue complementary to a second polynucleotide which is selected from the group consisting of HMGI genes, MAG genes and nucleic acid molecules having sequences according to one of SEQ ID NOS.: 1-19; and then (2) detecting significant complex formation between the first polynucleotide and the second polynucleotide when endometriosis is present, but not when endometriosis is absent. According to one embodiment of the invented method the first polynucleotide additionally comprises a marker or label.

An eighth aspect of the invention relates to a method for the diagnosis of endometriosis that includes the steps of: (1) administering to suspected ectopic endometrial tissue a translation product of a polynucleotide which is selected from the group consisting of HMGI genes, MAG genes and nucleic acid molecules having sequences according to one of SEQ ID NOS.: 1-19; and then (2) detecting significant complex formation between the translation product and the polynucleotide when endometriosis is present, but not when endometriosis is absent. According to one embodiment of the invented method, the translation product includes a marker or label.

A ninth aspect of the invention relates to a method for the diagnosis of endometriosis that includes the steps of: (1) administering to suspected ectopic endometrial tissue an antibody to a translation product of a polynucleotide selected from the group consisting of HMGI genes, MAG genes and nucleic acid molecules having sequences according to one of SEQ ID NOS.: 1-19; and then (2) detecting significant complex formation between the antibodies and the translation products when endometriosis is present, but not when endometriosis is absent. The antibody may be selected from the group consisting of polyclonal antibodies, monoclonal antibodies and fragments and derivatives thereof. In a preferred embodiment, the antibody includes a marker or label.

A tenth aspect of the invention relates to a method for contraception in a mammal which includes the steps of: (1) administering to the mammal a first polynucleotide complementary to a second polynucleotide selected from the group consisting of HMGI genes, MAG genes and nucleic acid molecules having sequences according to one of SEQ ID NOS.: 1-19; and then (2) forming a complex between said first polynucleotide and said second polynucleotide, thereby inhibiting fertility.

An eleventh aspect of the invention relates to a method for contraception in a mammal which includes the steps of: (1) administering to the mammal a translation product of a polynucleotide selected from the group consisting of HMGI genes, MAG genes and nucleic acid molecules having sequences according to one of SEQ ID NOS.: 1-19; and then (2) forming a complex between the translation product and the polynucleotide, thereby inhibiting fertility.

A twelfth aspect of the invention relates to a method for contraception in a mammal which includes the steps of: (1) administering to the mammal an antibody to a translation product of a polynucleotide selected from the group consisting of HMGI genes, MAG genes and nucleic acid molecules having sequences according to one of SEQ ID NOS.: 1-19; and then (2) forming a complex between the antibodies and the translation products, thereby inhibiting fertility. In a preferred embodiment, the antibody is selected from the group consisting of polyclonal antibodies, monoclonal antibodies and fragments and derivatives thereof.

A thirteen aspect of the invention relates to a method for regenerating tissue which includes the step of activating expression in the tissue of a nucleic acid sequence selected from the group consisting of HMGI genes, MAG genes, nucleic acid sequences according to SEQ ID Nos. 1-19 and their derivatives in a cell. The activating step may involve administering a phorbol ester. Alternatively, the activating step may involve administering the nucleic acid sequence in a vector. This nucleic acid sequence can be under transcriptional control of a promotor, and the promoter may be inducible. If the promoter is inducible then the administering step additionally may involve administering an agent which induces the promoter. According to another embodiment of the invention, tissue regeneration occurs in situ. According to a different embodiment, tissue regeneration is achieved by first carrying out the activating step in a cell which is then further propagated. In a preferred embodiment of the invented method the tissue to be regenerated is mesenchymal tissue. In one embodiment of the invention, the mesenchymal tissue is selected from the group comprising cartilage tissue, muscle tissue, fatty or adipose tissue, connective tissue and supporting tissue.

A fourteenth aspect of the invention relates to a method for regenerating tissue which involves administering to the tissue a translation product of a nucleic acid sequence selected from the group consisting of HMGI genes, MAG genes, nucleic acid sequences according to SEQ ID Nos. 1-19 and their derivatives. In one embodiment, the translation product is administered via an encapsulation technique to said tissue. In a different embodiment the tissue is regenerated by first carrying out the administering step to a cell which is then further propagated. According to yet another embodiment of the invention the tissue regeneration is performed in situ. The tissue to be regenerated particularly may be mesenchymal tissue. When the regeneration is performed in situ, the mesenchymal tissue can be selected from the group consisting of cartilage tissue, muscle tissue, fatty or adipose tissue, connective tissue and supporting tissue.

A fifteenth aspect of the invention relates to a method for inducing angiogenesis which includes the step of activating expression in venous or capillary tissue of a nucleic acid sequence selected from the group consisting of HMGI genes, MAG genes, nucleic acid sequences according to SEQ ID Nos. 1-19 and their derivatives in a cell. In one embodiment, the activating step involves administering a phorbol ester. In another embodiment, the activating step involves administering the nucleic acid sequence in a vector. This nucleic acid sequence can be under transcriptional control of a promotor. This promoter may be an inducible promoter and the administering step additionally may involve administering an agent which induces the promoter. In yet another preferred embodiment of the invented method, angiogenesis occurs in situ. Angiogenesis can be achieved by first carrying out the activating step in a cell which is then further propagated. Another aspect of the invention relates to a method for improving the vascular supply of myocardial tissue damaged by myocardial infarction, which method involves inducing angiogenesis by activating expression in venous or capillary tissue of a nucleic acid sequence selected from the group consisting of HMGI genes, MAO genes, nucleic acid sequences according to SEQ ID Nos. 1-19 and their derivatives in a cell.

A sixteenth aspect of the invention relates to a method for inducing angiogenesis, comprising administering to venous or capillary tissue a translation product of a nucleic acid sequence selected from the group consisting of HMGI genes, MAG genes, nucleic acid sequences according to SEQ ID Nos. 1-19 and their derivatives. In a preferred embodiment, the translation product is administered via an encapsulation technique to said tissue. In another preferred embodiment angiogenesis occurs by first carrying out the administering step to a cell which is then further propagated. In still another preferred embodiment, angiogenesis occurs in situ. A related aspect of the invention relates to a method for improving vascular supply of myocardial tissue damaged by myocardial infarction. This method involves inducing angiogenesis by administering to venous or capillary tissue a translation product of a nucleic acid sequence selected from the group consisting of HMGI genes, MAG genes, nucleic acid sequences according to SEQ ID Nos. 1-19 and their derivatives.

A seventeenth aspect of the invention relates to a method for inhibiting angiogenesis in a mammal. This method involves first administering to the mammal a first polynucleotide complementary to a second polynucleotide selected from the group consisting of HMGI genes, MAG genes and nucleic acid molecules having sequences according to one of SEQ ID NOS.: 1-19; and then forming a complex between the first polynucleotide and the second polynucleotide, thereby inhibiting angiogenesis. A related aspect of the invention regards a method of preventing or treating loss of sight as a consequence of neovascularization by inhibiting angiogenesis according to method involves first administering to the mammal a first polynucleotide complementary to a second polynucleotide selected from the group consisting of HMGI genes, MAG genes and nucleic acid molecules having sequences according to one of SEQ ID NOS.: 1-19; and then forming a complex between the first polynucleotide and the second polynucleotide, thereby inhibiting angiogenesis.

An eighteenth aspect of the invention relates to a method for inhibiting angiogenesis in a mammal which involves the steps of administering to the mammal a translation product of a polynucleotide selected from the group consisting of HMGI genes, MAG genes and nucleic acid molecules having sequences according to one of SEQ ID NOS.: 1-19; and then forming a complex between the translation product and the polynucleotide, thereby inhibiting angiogenesis. A related aspect of the invention regards a method of preventing or treating loss of sight as a consequence of neovascularization, which method involves inhibiting angiogenesis by administering to the mammal a translation product of a polynucleotide selected from the group consisting of HMGI genes, MAG genes and nucleic acid molecules having sequences according to one of SEQ ID NOS.: 1-19; and then forming a complex between the translation product and the polynucleotide, thereby inhibiting angiogenesis.

A nineteenth aspect of the invention relates to a method for inhibiting angiogenesis in a mammal which includes the steps of first administering to the mammal an antibody to a translation product of a polynucleotide selected from the group consisting of HMGI genes, MAG genes and nucleic acid molecules having sequences according to one of SEQ ID NOS.: 1-19; and then forming a complex between the antibodies and the translation products, thereby inhibiting angiogenesis. In one embodiment of the invented method the antibody is selected from the group consisting of polyclonal antibodies, monoclonal antibodies and fragments and derivatives thereof. A related aspect of the invention regards a method of preventing or treating loss of sight as a consequence of neovascularization which involves inhibiting angiogenesis by administering to the mammal an antibody to a translation product of a polynucleotide selected from the group consisting of HMGI genes, MAG genes and nucleic acid molecules having sequences according to one of SEQ ID NOS.: 1-19; and then forming a complex between the antibodies and the translation products, thereby inhibiting angiogenesis.

DETAILED DESCRIPTION OF THE PREFERRED EMBODIMENT

Figure 1:
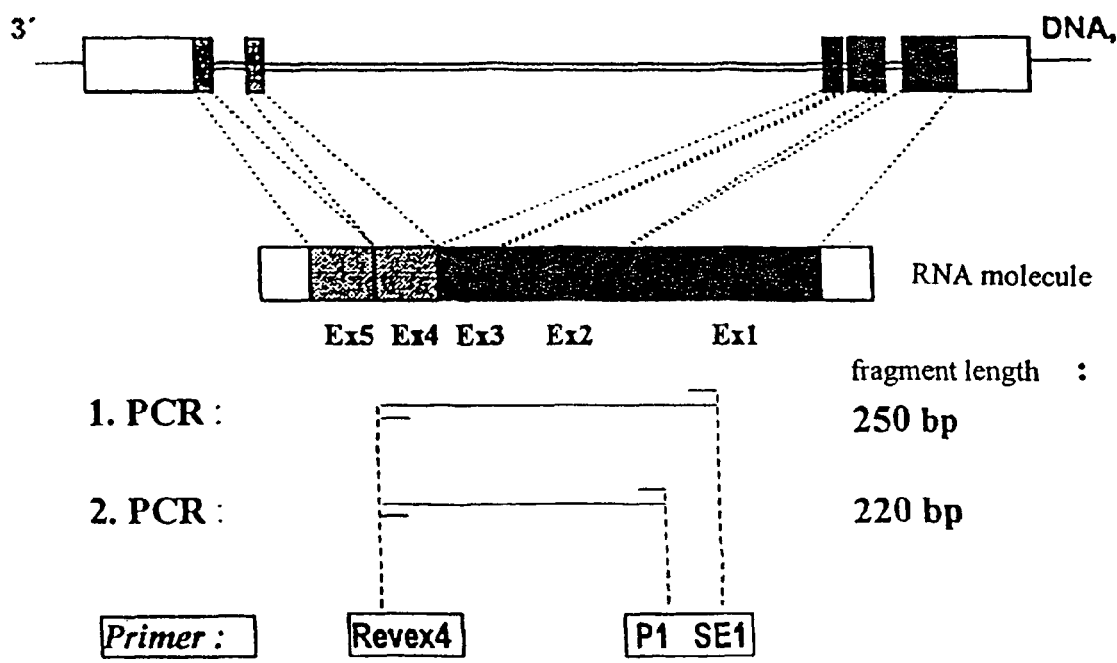
FIG. 1 is a diagram showing the genomic structure of the HMGI-C gene, RNA and cDNA and position of the primers used for the RT-PCR.

The mutations that can manifest themselves cytogenetically as structural chromosome aberrations of region q14-15 of chromosome 12, can be proven with the help of the methods of the polymerase chain reaction for the rapid amplification of 3' cDNA ends (3' RACE PCR) and/or for fluorescence in situ-hybridization. It is found that often breaks occur in the third and more rarely in the fourth intron of the HMGI-C gene. The 3' component of the gene is separated from its original sequence due to breaks and is substituted by a so-called ectopic DNA sequence. Such ectopic sequences apparently originate in other genes. The fusion gene of the ectopic sequence with parts of the HMGI-C that codes for the DNA-bonding components remains on the resulting derivative of chromosome 12 and is expressed as a fusion transcript in the cells, together with the original transcript. It is not known whether only an expression of the gene, e.g. caused by the shift of an enhancer in the area of the gene, can result in the growth of a tumor.

It is remarkable that many of the above tumors have subgroups for which the chromosome changes of band 6p21 are characteristic. The gene for HMGI-Y is located in this band, which, as already indicated above, has the highest homologous degree of all known HMG genes compared to the HMGI-C gene, so that mutations of this gene may also play a role in many of the above tumors.

The agents described in the state of the art that are used for the purpose of influencing angioneoplasm, i.e. (neo-)angiogenesis, (neo-)vascularization and tumor angiogenesis, and for the purpose of preventing blindness due to neo-vascularization as often occurs in connection with diabetes mellitus, for example, and for the purpose of treating endometriosis, for the purpose of contraception and tissue regeneration, are characterized in that they use an indirect mechanism to arrive at their final effect.

Indirect mechanism means that the respective agent itself, or effector molecules formed or activated by this agent, act on the target cells, possibly while using receptors or more or less specific receptor-like structures, and interfere in the cellular activity without carrying any specificity inherent in their own structure which would make it possible to influence the translation and/or the transcription of the gene or the sequences that are responsible for the respective phenomenon or clinical picture.

A number of basic disadvantages can be deducted from this mechanism. Due to non-specific receptor mechanisms or cross-reactivities of the receptors or receptor-like structures, said agents often are accepted into other tissues as target tissue or target cells. This is why there are no specific effective locations and therefore significant side-effects must be anticipated. In addition, the influence of said agents on the reactions within the cell results in a considerable disturbance which may or may not result in the desired effect in the target cell.

Especially problematic is influencing angioneoplasm with state of the art agents. Apart from the hope of spontaneous healing, the only other common option in clinical scenarios is to transplant vessels. The availability of suitable vessels is a very basic problem.

Influencing angioneoplasm in order to prevent tumor angiogenesis seems to be a promising prospect for an effective cancer therapy that is being examined using suitable, but typically systemic agents. The use of such systemic agents, however, is accompanied by corresponding negative effects, as described above and as they result from similarly non-specific radiation therapy.

There are numerous causes for the loss of vision and an equal number of different treatments are available today. It is a known fact that the vision of patients that suffer from diabetes mellitus is impaired due to neo-vascularization that can result in total blindness. It is possible to slow vision loss by treating the diabetes mellitus; however, there is an urgent need for an agent that specifically makes it possible to treat or prevent blindness due to neo-vascularization, independent of the therapy for diabetes mellitus.

The side-effects of hormonal agents used for contraceptive purposes are sufficiently known and, despite intensive efforts on the part of the drug companies, still exist. A central problem in the development of oral contraceptives certainly is the fact that there still is a need for a well tolerable and reliable agent that interrupts a pregnancy following the nidation of the fertilized egg.

Finally, tissue regeneration still is a largely unsolved problem despite successes, above all in the area of skin culture. Typically, complex nutrient solutions are used in order to regenerate at least some tissues. However, the ability to reproduce the process is not always certain, due to the complex media or complex media admixtures that are used whereby complex media or media admixtures are necessary because a targeted admixture of individual factors is rarely successful. Even if individual compositions are known that would allow for the regeneration of the respective tissue in the desired manner, side-effects have to be anticipated as well, due to the indirect action of such compositions. In addition, the person responsible for regenerating the tissue, as well as the patient who is to receive the regenerated tissue, might be at great risk due to the biological sources required for the regeneration process.

The treatment of tumors still poses one of the greatest challenges to medicine. Despite comprehensive efforts, there are few specific therapies. Often chemotherapy and radiation therapy offer the only alternatives, but they have inherent side-effects that often question the use of the therapies as such.

The invention is charged with describing and making available DNA sequences that are suitable, for example, for providing agents for the purpose of treating diseases or for the purpose of influencing biological systems while reducing the side-effects that are usually associated with such treatments.

Another object of the invention is to show new uses of sequences of the MAG genes or the genes of the high mobility group proteins, and to provide agents for the specific treatment of diseases or for influencing biological systems, while reducing the side-effects that are usually associated with them. The object of the invention is attained through a DNA sequence that is characterized by at least one sequence as shown in SEQ ID NOs: 1 through 19.

In one of the embodiments the DNA sequence corresponds partially or completely to the sequence of the HMGI-C gene.

In another embodiment of the invention, parts of the sequences shown in SEQ ID NOs: 1 through 19 make up a part of the DNA sequence of the HMGI-C gene.

It is possible for the DNA sequence to be mutant as compared to the DNA sequence shown in SEQ ID NOs: 1 through 19.

The invention proposes that the DNA sequence primarily has the same sequence as the one shown in SEQ ID NOs: 1 through 19, including the respective complementary strand and modified versions of both strands.

An alternative is that the DNA sequence has a primarily functionally identical nucleic acid sequence to the sequences shown in SEQ ID NOs: 1 through 19.

In one embodiment, the DNA sequence in accordance with the invention has at least one sequence that codes for a DNA-bonding part of the corresponding translation product(s).

An alternative is that the sequence in accordance with the invention does not have a sequence that codes for the protein-bonding part of the corresponding translation product(s).

In a preferred embodiment, the sequence in accordance with the invention has one or several sequences $S_r$ which replace(s) or supplement(s) the sequence(s) that code(s) for the protein-bonding part of the corresponding translation product(s).

In an especially preferred embodiment sequence, $S_r$ is selected from the group that comprises other sequences of the human genome, sequences of other (donor) organisms and artificial sequences and combinations thereof.

In an alternative embodiment, the sequences shown in SEQ ID NOs: 1 through 19 are aberrant transcripts of the HMGI-C gene.

In the following paragraphs the above sequences will be called $S_{AT}$.

The invention also describes an expression vector that comprises at least one transcription promoter that is followed by at least one of the $S_{AT}$ sequences further down.

In addition, the invention comprises a host cell that transfers or transforms with an expression vector in accordance with the invention.

In a preferred embodiment the host cell is a prokaryotic cell.

In yet another embodiment the host cell is an eukaryotic cell.

In a preferred embodiment the eukaryotic cell is a yeast cell.

In an especially preferred embodiment, the eukaryotic cell is a mammal cell.

In addition, the invention describes a protein that is a translation product of one or several of the $S_{AT}$ sequences and/or the corresponding transcript(s) in native or mutant form and/or in a complete or fragmented form whereby the translation product glycosylates, is native or mutant and/or is in a complete or fragmented state, glycosylates partially or not at all and/or phosphorylates or does not phosphorylate and/or is chemically modified or not chemically modified.

In yet another aspect the object of the invention is attained through the use of at least one of the $S_{AT}$ sequences in accordance with the invention for the purpose of influencing angioneoplasm.

The invention also describes another aspect that attains the object of the invention through the use of a MAG gene for the purpose of influencing angioneoplasm.

Another aspect that attains the object of the invention is the use of at least one high mobility group protein gene for the purpose of influencing angioneoplasm.

In a preferred embodiment, the high mobility group protein gene is selected from the group that comprises the HMGI-C gene and the HMGI-Y gene.

In the following paragraphs the above genes or groups of genes will be referred to as $G_G$.

It is possible to use sequences that have fundamentally the same nucleic acid sequence as the $G_G$ genes.

An alternative is the use of sequences that have essentially the same functional nucleic acid sequence as that of the $G_G$ genes.

In the following paragraphs, the above defined sequences together with the above defined $G_G$ genes will be referred to as $S_G$ sequences.

In another embodiment, the $S_G$ sequences have at least one sequence that codes for a DNA-bonding component of the corresponding translation product(s).

In another alternative of the invention the $S_G$ sequences and their derivatives in accordance with the invention do not have any of the sequences that code for the protein-bonding component of the corresponding translation product(s).

In addition, the $S_G$ sequences or derivatives in accordance with the invention have one or several $S_r$ sequences that replace(s) or supplement(s) the sequence(s) that code(s) for the protein-bonding component of the corresponding translation product(s).

It is possible for the $S_r$ sequence to be selected from the group that comprises other sequences of the human genome, sequences of other (donor) organisms, and artificial sequences and combinations thereof.

In one embodiment the $S_{AT}$ and $S_G$ sequences and their derivatives in accordance with the invention are double-strands and/or a coding and/or non-coding single strand and/or cDNA.

The $S_{AT}$ and $S_G$ sequences and their derivatives in accordance with the invention can be native and/or mutant and/or in a fragmented or non-fragmented state.

In an embodiment of the invention the $S_{AT}$ and $S_G$ sequences and their derivatives in accordance with the invention can have at least one promoter and/or at least one enhancer element and/or at least one transcription termination element and/or at least one resistance gene and/or at least one additional marking gene.

In one embodiment at least one of the $S_{AT}$ or $S_G$ sequences or their derivatives in accordance with the invention can be cloned in a host system.

In this case the $S_{AT}$ and $S_G$ sequences and their derivatives in accordance with the invention are copied at least once.

In the following paragraphs the above $G_G$ genes, the $S_G$ sequences and their derived sequences or the different embodiments will be referred to as $S_T$ sequences.

In accordance with the invention the object of the invention is attained with the help of an agent used for the purpose of influencing angioneoplasm and that is comprised of at least one agent $M_S$ that is selected from the group that comprises sense DNA, sense RNA, sense cDNA, antisense DNA, antisense RNA and antisense cDNA and combinations thereof as a single strand and/or double strand.

It may be possible for the sequence(s) of the agent(s) $M_S$ to be native or mutant and/or in a complete or a fragmented state and/or chemically modified or not chemically modified.

In a preferred embodiment of the invention the sequence of the $M_S$ agent(s) correspond(s) to a or several $S_T$ or $S_{AT}$ sequence(s) and/or the corresponding transcript(s) that is(are) native or mutant and in a complete or fragmented state.

In the subsequent paragraphs the agents selected from the group that comprises the nucleic acid will be referred to as $M_{MAKS}$ agents.

In addition, the object of the invention is attained with the help of an agent used for the purpose of influencing angioneoplasm that comprises at least one agent $M_P$ that is selected from the group that comprises poly-clonal antibodies, monoclonal antibodies, and fragments and derivatives thereof.

In this case it is especially preferred if the $M_P$ agent acts against a $S_T$ or $S_{AT}$ sequence(s) and/or the corresponding transcription product(s) that is(are) native or mutant and/or in a complete or fragmented state.

In an especially preferred embodiment the $M_P$ agent acts against one or several translation products of a $S_T$ or $S_{AT}$ sequence or several sequences and/or the corresponding transcript(s) that is(are) native or mutant and/or in a complete or fragmented state and whereby said translation product(s) is(are) native or mutant and/or in a complete or fragmented state and/or is(are) glycosylated, partially glycosylated or not glycosylated and/or is(are) phosphorylated or not phosphorylated.

In addition, within the framework of the invention, agent $M_P$ in accordance with the invention acts against an antibody or a fragment of an antibody which in turn acts against one or several $S_T$ or $S_{AT}$ sequences and/or the translation product(s) and/or the corresponding transcription product(s) that is(are) native or mutant and/or in a complete or fragmented state.

In addition, it is possible for agent $M_P$ in accordance with the invention to act against an antibody or a fragment of the antibody which in turn acts against one or several translation products of one or several of the $S_T$ or $S_{AT}$ sequences and/or the corresponding transcript(s) that is(are) native or mutant and/or in a complete or fragmented state and whereby said translation product(s) is(are) native or mutant and/or in a complete or fragmented state and/or is(are) glycosylated, partially glycosylated or not glycosylated and/or is(are) phosphorylated or not phosphorylated.

In the subsequent paragraphs the above agents selected from the group of antibodies and fragments and their derivatives will be referred to as $M_{MAKP}$ agents.

In accordance with the invention the object is also attained with the help of an agent used for the purpose of influencing angioneoplasm that is comprised of at least one translation product of one or several $S_T$ or $S_{AT}$ sequences and/or the corresponding transcript(s) that is(are) native or mutant and/ or in a complete or fragmented state and whereby said translation product(s) is(are) native or mutant and/or in a complete or fragmented state and/or is(are) glycosylated, partially glycosylated or not glycosylated and/or is(are) phosphorylated or not phosphorylated and/or is(are) chemically modified or not chemically modified.

In the subsequent paragraphs the above translation product will be referred to as translation product TP.

Finally the object of the invention is attained with the help of an agent in accordance with the invention that is used for the purpose of influencing angioneoplasm and that is comprised of at least one expression inhibitor and/or at least an agent that stimulates the expression.

Especially preferred in this case is when the expression inhibitor and/or the agent that stimulates the expression has a higher degree of specificity for one or several of the $S_T$ or $S_{AT}$ sequences compared to other genes of the respective genetic system.

Especially preferred is a scenario in which the expression inhibitor and/or the agent that stimulates the expression is specific for one or several $S_T$ or $S_{AT}$ sequences.

The above described expression inhibitor will be referred to as expression inhibitor I and the above described agent that stimulates the expression will be referred to as agent ES.

One use of the agent in accordance with the invention for the purpose of influencing angioneoplasm concerns angiogenesis.

Especially preferred is an effect which reduces and/or prevents angiogenesis.

In an alternative, angiogenesis can be stimulated.

Especially preferred is an embodiment in which the influence on the angioneoplasm affects tumor angiogenesis.

In addition, one use of the agents in accordance with the invention for the purpose of influencing angioneoplasm concerns vascularization.

Especially preferred in this case is an embodiment in which vascularization is stimulated.

As alternative is for vascularization to be reduced or prevented.

Another aspect of the invention concerns the treatment and/or prevention of blindness due to neo-vascularization while using at least one of the agents in accordance with the invention for the purpose of influencing angioneoplasm.

Finally another aspect of the invention is to improve the vessel supply of heart muscle tissue with cardiac infarction damage while using at least one agent in accordance with the invention for the purpose of influencing angioneoplasm.

It is possible to use the agent in accordance with the invention in humans and/or animals.

In addition, it is possible to use the agent for therapeutic and/or diagnostic applications in humans and/or animals.

In addition, it is possible to use it in vitro.

Another use in accordance with the invention of at least one of the agents in accordance with the invention is its/their use in the production of a drug for therapeutic and/or diagnostic applications for the purpose of influencing angioneoplasm.

Another aspect of the invention describes a kit for the purpose of influencing angioneoplasm that contains at lest one $M_{MAKS}$ and/or one $M_{MAKP}$ agent.

It is possible for the kit to contain at least one translation product of one or several of the $S_T$ or $S_{AT}$ sequences and/or the corresponding transcript(s) that is(are) native or mutant and/or or in a complete or fragmented state and whereby said translation product(s) is(are) native or mutant and/or in a complete or fragmented state and/or is(are) glycosylated, partially glycosylated or not glycosylated and/or is(are) phosphorylated or not phosphorylated and/or is(are) chemically modified or not chemically modified.

At least one expression inhibitor I and/or at least one agent ES that stimulates the expression is contained in one embodiment of the kit.

In an especially preferred embodiment of the invention the kit contains at least one $M_{MAKS}$ and/or at least one $M_{MAKP}$ agent and/or one translation product TP and/or at least one expression inhibitor I and/or at least an agent ES that stimulates the expression.

In an especially preferred embodiment the kit can be used for the purpose of influencing tumor angiogenesis.

In another embodiment the kit is used for the purpose of influencing angiogenesis.

It also is possible to use the kit for the purpose of influencing vascularization.

An alternative is to use the kit for the purpose of inhibiting angioneoplasm.

An alternative is to use the kit for the purpose of stimulating angioneoplasm.

Finally, it is possible to use the kit for the purpose of treating and/or preventing blindness due to neo-vascularization.

In addition, it is possible to use the kit in accordance with the invention for the purpose of improving the vessel supply of heart muscle tissue damaged by cardiac infarction.

The kit may be used for therapeutic treatment and/or for diagnosis purposes.

It is possible to use the kit in humans and/or animals.

Finally it is possible to use the kit in in vitro systems.

The object is attained in accordance with the invention through the use of at least one of the sequences $S_{AT}$ in accordance with the invention for the treatment of endometriosis.

In a broader aspect in which the object is attained, the invention concerns the use of a MAG gene for the treatment of endometriosis.

A further aspect of the invention in which the object is attained concerns the use of at least one high mobility group protein gene for the treatment of endometriosis.

In a preferred embodiment, it is provided that the high mobility group protein gene is selected from the group which comprises the HMGI-C gene and the HMGI-Y gene.

The above genes and/or groups of genes are designated below as genes $G_G$.

It can be provided that sequences are used with essentially the same sequence of nucleic acid as the gene $G_G$.

In an alternative, sequences can be used with a nucleic sequence which is essentially the same functionally as that of the gene $G_G$.

The above-defined sequences together with the above-defined genes $G_G$ will be designated below as sequences $S_G$.

In a further embodiment, it is provided that the sequences $S_G$ have at least one sequence which codes for a DNA binding portion of the corresponding translation product(s).

In a further alternative of the invention, it is provided that the sequences $S_G$ and derivatives thereof do not have any sequence which codes for the protein-binding portion of the corresponding translation product(s).

It can further be provided that the sequences $S_G$ or derivatives thereof in accordance with the invention have one or several sequences $S_r$ which replace the sequence(s) which code for the protein-binding portion of the corresponding translation product(s).

It is possible in this case for the sequence $S_r$ to be selected from the group which comprises other sequences of the human genome, sequences of other (donor) organisms, and artificial sequences and combinations thereof.

In one embodiment, it is provided that the sequences $S_{AT}$ or $S_G$, as well as derivatives thereof in accordance with the invention are present as double-strand and/or coding and/or non-coding single strand and/or cDNA.

It can further be provided that the sequences $S_{AT}$ or $S_G$ as well as derivatives thereof in accordance with the invention are present in native and/or mutant and/or fragmented or unfragmented forms.

In one embodiment of the invention, the sequences $S_{AT}$ or $S_G$ as well as derivatives thereof in accordance with the invention have at least one enhancer element and/or at least one transcription termination element and/or at least one resistance gene and/or at least one other marking gene.

In one embodiment, at least one of the sequences $S_{AT}$ or $S_G$ or derivatives thereof in accordance with the invention are present as clones in a host system.

It is provided in this case that the sequences $S_{AT}$ or $S_G$ or derivatives thereof in accordance with the invention are present in at least one copy.

The aforementioned gene $G_G$, the sequences $S_G$, and the sequences derived therefrom or the various embodiments are designated below as sequences $S_T$.

The object is attained in accordance with the invention through an agent for the treatment of endometriosis which comprises at least one agent $M_S$; which is selected from the group which comprises sense DNA, sense RNA, sense cDNA, antisense DNA, antisense RNA, and antisense cDNA, and combinations thereof as individual strands and/or double strands.

It can be provided that the sequence(s) of the agent(s) $M_S$ are present in native or mutant form and/or complete or fragmented and/or chemically modified or not chemically modified.

In a preferred embodiment, the sequence of the agent(s) $M_S$ correspond to sequence(s) $S_T$ or the corresponding transcript(s) which are present in native or mutant form, complete or fragmented.

The above agents selected from the group comprising the nucleic acids shall be referred to below as agents $M_{MAKS}$.

The object is further attained through an agent for the treatment of endometriosis which comprises at least one agent $M_P$ which is selected from the group which comprises polyclonal antibodies, monoclonal antibodies, and fragments and derivatives of the same.

It is especially preferred In this case that the agent $M_P$ be directed against a sequence(s) $S_T$ or $S_{AT}$ and/or the corresponding transcription product(s) which are present in native or mutant form and/or complete or fragmented.

In a particularly preferred embodiment, the agent $M_P$ acts against one or several translation products of a sequence or several sequences $S_T$ or $S_{AT}$ and/or of the corresponding transcript(s) which are present in native or mutant form and/or complete or fragmented and whereby said translation product(s) are present in native or mutant form and/or complete or fragmented and/or glycosylated, partially glycosylated, or not glycosylated and/or phosphorylated or not phosphorylated.

In addition, it is within the framework of the present invention that the agent $M_P$ in accordance with the invention acts against an antibody or a fragment thereof which in turn acts against one or more sequences $S_T$ or $S_{AT}$ and/or the corresponding transcription product(s) which are present in native or mutant form and/or complete or fragmented.

In addition, it can be provided that the agent in accordance with the invention act against an antibody or a fragment of the same which in turn acts against one or several translation products of one or several sequences $S_T$ or $S_{AT}$ and/or corresponding transcript(s) which are present in native or mutant form and/or complete or fragmented and whereby said translation product(s) are present in native or mutant form and/or complete or fragmented and/or glycosylated, partially glycosylated or not glycosylated and/or phosphorylated or not phosphorylated.

The aforementioned agent selected from the group comprised of antibodies and fragments and derivatives of the same will be designated below as agent $M_{MAKP}$.

The object is attained in accordance with the invention through an agent which comprises at least one translation product of one or several sequences $S_T$ or $S_{AT}$ and/or the corresponding transcript(s) which are present in native or mutant form and/or complete or fragmented and whereby said translation product(s) are present in native or mutant form and/or complete or fragmented and/or glycosylated, partially glycosylated or not glycosylated and/or phosphorylated or not phosphorylated and/or chemically modified or not chemically modified.

The translation product described above shall be designated below as translation product TP.

Finally, the object is attained by means of an agent in accordance with the invention for the treatment of endometriosis which comprises at least one expression inhibitor and/or at least one agent which stimulates the expression.

It is particularly preferred In this case that the expression inhibitor and/or the expression stimulating agent have an elevated specificity for one or more of the sequences $S_T$ or $S_{AT}$ compared with other genes of the genetic system in question.

It is quite particularly preferred In this case that the expression inhibitor and/or the expression-stimulating agent be specific for one or more sequences $S_T$ or $S_{AT}$.

One application in accordance with the invention provides that at least one of the agents in accordance with the invention is used for the treatment of endometriosis in humans or in animals.

In one embodiment, use is indicated for therapeutic and/or diagnostic application in humans and/or in animals.

A further application in accordance with the invention provides the in vitro application of at least one of the agents in accordance with the invention.

Finally, an application in accordance with the invention can provide for the application of at least one of the agents in accordance with the invention for the manufacture of a drug for the therapeutic and/or diagnostic application in the treatment of endometriosis.

In a further aspect, the invention concerns a kit for the treatment of endometriosis which contains at least an agent $M_{MAKS}$ and/or an agent $M_{MAKP}$.

It is possible for a kit to contain a translation product of one or more of sequences $S_T$ or $S_{AT}$ and/or of the corresponding transcript(s) which are present in native or mutant form and/or complete or fragmented and whereby said translation product(s) are present in native or mutant form and/or complete or fragmented and/or glycosylated, partially glycosylated or not glycosylated and/or phosphorylated or not phosphorylated and/or chemically modified or not chemically modified.

In one embodiment of the kit, at least one expression inhibitor I and/or one expression-stimulating agent ES are contained.

In a particularly preferred embodiment, it is provided that at least one agent $M_{MAKS}$ and/or at least one agent $M_{MAKP}$ and/or at least one translation product TP and/or at least one expression inhibitor I and/or at least one expression-stimulating agent ES is contained.

The kit can be used for therapeutic treatment and/or for diagnosis.

It is provided that the kit will be used with humans and/or animals.

Finally, the kit can also be used in in vitro systems.

The object can be attained in accordance with the invention through the use of at least one of the sequences $S_{AT}$ for contraception.

In a broader aspect in which the object is attained, the invention concerns the use of a MAG gene for contraception.

Another aspect of the invention in which the object is attained concerns the use of at least one high mobility group protein gene for contraception.

In a preferred embodiment, it is provided that the high mobility group protein gene is selected from the group which comprises the HMGI-C gene and the HMGI-Y gene.

The above gene or group of genes are designated below as genes $G_G$.

It can be provided that sequences are used with essentially the same nucleic acid sequence as the genes $G_G$.

In an alternative, sequences can be used with nucleic acid sequence which is, in essence, functionally the same as that of genes $G_G$.

The sequences defined above, together with genes $G_G$, which are likewise defined above, shall be designated from this point forward as sequences $S_G$.

In a further embodiment, it is provided that the sequences $S_G$ have at least one sequence which code for a DNA-binding portion of the corresponding translation product(s).

In a further alternative of the invention, it is provided that the sequences $S_G$ and derivatives thereof have no sequence which codes for the protein-binding portion of the corresponding translation product(s).

Furthermore, it can be provided that the sequences $S_G$ or derivatives thereof in accordance with the invention have one or more sequences $S_r$ which replace or supplement that sequence or those sequences which code for the protein-binding portion of the corresponding translation product(s).

It is possible in this case for the sequences $S_r$ to be selected from the group which comprises the other sequences of the human genome, sequences of other (host) organisms, and artificial sequences and combinations thereof.

In one embodiment, it is provided that the sequences $S_{AT}$ and $S_G$ as well as derivatives thereof in accordance with the invention are present as double strand and/or coding and/or non-coding single strand and/or cDNA.

Furthermore, it can be provided that the sequences $S_{AT}$ and $S_G$ as well as derivatives thereof in accordance with the invention are present as natives and/or mutants and/or fragmented or not fragmented.

In one embodiment of the invention, the sequences $S_{AT}$ and $S_G$ as well as derivatives thereof have at least one promoter and/or at least one enhancer element and/or at least one transcription termination element and/or at least one resistance gene and/or at least one other marking gene.

In one embodiment, at least one of the sequences $S_{AT}$ or $S_G$ or derivatives in accordance with the invention are present as clones in a host system.

It is provided in this case that the sequences $S_{AT}$ and $S_G$ as well as derivatives thereof in accordance with the invention are present in at least one copy.

The aforementioned genes $G_G$, the sequences $S_G$, and the sequences derived therefrom or from the various embodiments are designated below as sequences $S_T$.

The object is attained in accordance with the invention through an agent for contraception which comprises at least one agent $M_S$ which is selected from the group which comprises sense DNA, sense RNA, sense cDNA, antisense DNA, antisense RNA, and antisense cDNA and combinations thereof as single strand and/or as double strand.

It can be provided that the sequence(s) of the agent(s) $M_S$ are present in native or mutant form and/or complete or fragmented and/or chemically modified or not chemically modified.

In a preferred embodiment, the sequence of the agent(s) $M_S$ correspond to a sequence(s) $S_T$ or $S_{AT}$ and/or to the corresponding transcript(s) which is present in native or mutant form, complete or fragmented.

The aforementioned agents derived from the group comprising nucleic acids shall be designated below as agent $M_{MAKS}$.

The object can also be attained through an agent for contraception which comprises at least one $M_S$ which is selected from the group which comprises polyclonal antibodies, monoclonal antibodies, and fragments and derivatives of the same.

It is particularly preferred In this case that the agent $M_P$ act against the sequence(s) $S_T$ or $S_{AT}$ and/or the corresponding transcription product(s) which are present in native or mutant form and/or complete or fragmented.

In a particularly preferred embodiment, the agent $M_P$ acts against one or more translation products of one or more sequences $S_T$ or $S_{AT}$ and/or of the corresponding transcript(s) which are present in native or mutant form and/or complete or fragmented and whereby said translation product(s) are present in native or mutant form and/or compete or fragmented and/or glycosylated, partially glycosylated, or not glycosylated and/or phosphorylated or not phosphorylated.

Furthermore, it is within the framework of the present invention that the agent $M_P$ in accordance with the invention acts against an antibody or a fragment of the same which in turn acts against a sequence(s) $S_T$ or $S_{AT}$ and/or the corresponding transcription product(s) are present in native or mutant form and/or complete or fragmented.

Furthermore, it can be provided that the agent $M_P$ in accordance with the invention acts against an antibody or a fragment of the same which in turn acts against one or several translation products of one or more sequences $S_T$ or $S_{AT}$ and/or of the corresponding transcript(s) which are present in native or mutant form and/or complete or fragmented, and whereby said translation product(s) are present in native or mutant form and/or complete or fragmented and/or glycosylated, partially glycosylated, or not glycosylated and/or phosphorylated or not phosphorylated.

The above-indicated agents selected from the group comprising the antibodies and fragments and derivatives of the same will be designated below as agents $M_{MAKP}$.

The object is attained in accordance with the invention through an agent for contraception which comprises at least one translation product(s) or one or more sequences $S_T$ or $S_{AT}$ and/or of the corresponding transcript(s) which are present in native or mutant form and/or complete or fragmented and whereby said translation product(s) are present in native or mutant form and/or complete or fragmented and/or glycosylated, partially glycosylated, or not glycosylated and/or phosphorylated or not phosphorylated and/or chemically modified or not chemically modified.

The above described translation product is designated below as translation product TP.

Finally, the object is attained through an agent in accordance with the invention for contraception which comprises at least one expression inhibitor and/or at least one agent which stimulates the expression.

It is particularly preferred in this case that the expression inhibitor and/or the agent which stimulates the expression have an elevated specificity for one or more of the sequences $S_T$ or $S_{AT}$ compared with other genes of the particular genetic system.

It is particularly preferred in this case that the expression inhibitor and/or the agent which stimulates the expression be specific for one or more sequences $S_T$ or $S_{AT}$.

The above described expression inhibitor will be designated below as expression inhibitor I and the above described expression-stimulating agent will be designated below as ES.

An application in accordance with the invention provides the application of at least one of the agents in accordance with the invention for oral contraception.

A further application in accordance with the invention provides the use of at least one of the agents in accordance with the invention for local contraception.

It can be provided that the application is for humans and/or for animals.

In an alternative, the application concerns the therapeutic application for humans and/or for animals.

A further application in accordance with the invention of at least one of the agents in accordance with the invention concerns the manufacture of a drug for therapeutic application.

In an additional application in accordance with the invention, the aspect through which the object is attained concerns the invention of a kit for contraception which contains at least one agent $M_{MAKS}$ and/or at least one agent $M_{MAKP}$.

It is possible for a kit to contain at least one translation product of one or more of the sequences $S_T$ or $S_{AT}$ and/or of the corresponding transcript(s) which are present in native or mutant form and/or complete or fragmented and whereby said translation product(s) in native or mutant form and/or complete or fragmented and/or glycosylated, partially glycosylated, or not glycosylated and/or phosphorylated or not phosphorylated and/or chemically modified or not chemically modified.

In one embodiment of the kit, at least one expression inhibitor I and/or at least one expressing-stimulating agent ES is contained.

In a particularly preferred embodiment, it is provided that at least one agent $M_{MAKS}$ and/or at least one agent $M_{MAKP}$ and/or at least one translation product TP and/or at least one expression inhibitor I and/or at least one expression-stimulating agent ES be contained in the kit.

In a quite particularly preferred embodiment, the kit can be used for oral contraception.

Furthermore, it is possible for the kit to be used for local contraception.

The kit can be used for therapeutic treatment and/or for diagnosis.

It is provided that the kit is used for humans and/or animals.

Finally, the kit can also be used in in vitro systems.

In a further aspect, the invention concerns a process of contraception which provides that at least one agent is administered which is selected from the group which contains sense DNA, sense RNA, sense cDNA, antisense DNA, antisense RNA, and antisense cDNA and combinations thereof as a single strand and/or as a double strand and whereby the sequence of the agent selected from the group corresponds to the sequence(s) $S_T$ and/or $S_{AT}$ and/or the corresponding transcript(s) which is(are) present in native or mutant form and/or complete or fragmented.

In addition, the invention represents a process for contraception which provides for the administration of at least one agent which is selected from the group which contains polyclonal antibodies, monoclonal antibodies, and fragments and derivatives of the same and whereby the agent selected from the group acts against the sequence(s) $S_T$ and/or $S_{AT}$ and/or in the direction opposite to the corresponding transcript(s) which are present in native or mutant form and/or complete or fragmented.

In a further aspect of the invention, a process for contraception is suggested which provides that at least one agent be administered which is selected from the group which contains polyclonal antibodies, monoclonal antibodies, and fragments and derivatives of the same and whereby the agent selected from the group acts against one or more of sequences $S_T$ and/or $S_{AT}$ and/or of the corresponding transcript(s) which is(are) present in native or mutant form and/or complete or fragmented and whereby said translation product(s) is(are) present in native or mutant form and/or complete or fragmented and/or glycosylated, partially glycosylated, or not glycosylated and/or phosphorylated or not phosphorylated.

In addition, the invention suggests a procedure for contraception which is characterized by the fact that at least one agent is administered which is a translation product of one or more sequences $S_T$ and/or $S_{AT}$ and/or of the corresponding transcript(s) which is(are) present in native or mutant form and/or complete or fragmented and whereby said translation product(s) is(are) present in native or mutant form and/or complete or fragmented and/or glycosylated, partially glycosylated, or not glycosylated and/or phosphorylated or not phosphorylated and/or chemically modified or not chemically modified.

In preferred embodiments of the process in accordance with the invention for contraception, said agent is administered orally.

In a further preferred embodiment, it is provided that said agent is administered periodically.

An additional alternative of the procedure in accordance with the invention provides that said agent is administered following conception.

The object is attained in accordance with the invention through the use of at least one of sequences $S_{AT}$ for tissue regeneration.

In a further aspect through which the object is attained, the invention concerns the use of a MAG gene for tissue regeneration.

Another aspect of the invention in which the object is attained concerns the use of at least one high mobility group protein gene for tissue regeneration.

In a preferred embodiment, it is provided that the high mobility group protein gene is selected from the group which comprises the HMGI-C gene and the HMGI-Y gene.

The above genes or groups of genes are designated below as gene $G_G$.

It can be provided that sequences are used with essentially the same nucleic acid sequence as genes $G_G$.

In an alternative, sequences are used with a nucleic acid sequence which is essentially the same functionally as that of the genes $G_G$.

The above-defined sequences together with the above-defined genes $G_G$ shall be designated below as sequences $S_G$.

In a further embodiment, it is provided that the sequences $S_G$ have at least one sequence which codes for a DNA-binding portion of the corresponding translation product(s).

In a further alternative of the invention, it is provided that the sequences $S_G$ and derivatives thereof do not have any sequence which codes for the protein-binding portion of the corresponding translation product(s).

Furthermore, it can be provided that the sequences $S_G$ or derivatives thereof in accordance with the invention have one or more sequences $S_r$ which replace or supplement that sequence or those sequences which code for the protein-binding portion of the corresponding translation product(s).

It is possible in this case for the sequence $S_r$ to be selected from the group which comprises other sequences of the human genome, sequences of other (host) organisms and artificial sequences and combinations thereof.

In one embodiment, it is provided that the sequences $S_{AT}$ or $S_G$ and derivatives in accordance with the invention thereof are present as double strand and/or coding and/or non-coding single strand and/or cDNA.

Furthermore, it can be provided that the sequences $S_{AT}$ of $S_G$ and the derivatives thereof in accordance with the invention are present as native and/or mutant and/or fragmented or not fragmented.

In one embodiment of the invention, the sequences $S_{AT}$ or $S_G$ and derivatives thereof in accordance with the invention can have at least one promoter and/or at least one enhancer element and/or at least one transcription termination element and/or at least one resistance gene and/or at least one other marking gene.

In one embodiment, at least one of the sequences $S_{AT}$ or $S_G$ or derivatives thereof in accordance with the invention are present as clones in a host system.

It is provided in this case that the sequences $S_{AT}$ or $S_G$ and derivatives thereof in accordance with the invention are present in at least one copy.

The above genes $G_G$, the sequences $S_G$, and the sequences derived therefrom or the various embodiments will be designated below as sequences $S_T$.

The object is attained in accordance with the invention through an agent for tissue regeneration which comprises at least one agent $M_S$ which is selected from the group which comprises sense DNA, sense RNA, sense cDNA, antisense DNA, antisense RNA, and antisense cDNA and combinations thereof as single strand or double strand.

It can be provided that the sequence(s) of agent(s) $M_S$ are present in native or mutant form and/or complete or fragmented and/or chemically modified or not chemically modified.

In a preferred embodiment, the sequence of agent(s) $M_S$ correspond to a sequence(s) $S_T$ or $S_{AT}$ and/or to the corresponding transcript(s) which are present in native or mutant form, complete or fragmented.

The above agents selected from the group comprised on nucleic acids are designated below as agents $M_{MAKS}$.

Furthermore, the object is attained in accordance with the invention through an agent for regeneration of tissue which comprises at least one agent $M_P$ which is selected from the group which comprises polyclonal antibodies, monoclonal antibodies, and fragments and derivatives of the same.

It is particularly preferred in this case that the agent $M_P$ be directed against a sequence(s) $S_T$ or $S_{AT}$ and/or the corresponding transcription product(s) which are present in native or mutant form and/or complete or fragmented.

In a particularly preferred embodiment, the agent $M_P$ acts against one or more translation products of a sequence or several sequences $S_T$ or $S_{AT}$ and/or of the corresponding transcripts which are present in native or mutant form and/or complete or fragmented and whereby said translation product(s) are present in native or mutant form and/or complete or fragmented and/or glycosylated, partially glycosylated, or not glycosylated and/or phosphorylated or not phosphorylated.

Furthermore, it is within the framework of the invention for the agent $M_P$ in accordance with the invention to be directed against an antibody or a fragment thereof which in turn acts against a sequence(s) $S_T$ or $S_{AT}$ and/or the corresponding transcription product(s) which are present in native or mutant form and/or complete or fragmented.

Furthermore, it can be provided that the agent $M_P$ in accordance with the invention acts against an antibody or a fragment thereof which in turn acts against one or more translation product(s) of a sequence(s) $S_T$ or $S_{AT}$ and/or of the corresponding transcript(s) which are present native or mutated and/or complete or fragmented and whereby said translation product(s) are present in native or mutant form and/or complete or fragmented and/or glycosylated, partially glycosylated, or not glycosylated and/or phosphorylated or not phosphorylated.

The above agents selected from the group comprising the antibodies and fragments and derivatives of the same are designated below as agents $M_{MAKP}$.

The object is attained in accordance with the invention through an agent for the regeneration of tissue which comprises at least one translation product of a sequence(s) $S_T$ or $S_{AT}$ and/or of the corresponding transcript(s) which is(are) present in native or mutant form and/or complete or fragmented and whereby said translation product(s) is(are) present in native or mutant form and/or complete or fragmented and/or glycosylated, partially glycosylated, or not glycosylated and/or phosphorylated or not phosphorylated and/or chemically modified or not chemically modified.

The above-described translation product is designated below as translation product TP.

Finally, the object is attained through an agent in accordance with the invention for regeneration of tissue which comprises at least one agent which stimulates the expression.

It is particularly preferred in this case that compared with other genes of the particular genetic system, the agent which stimulates the expression have an elevated specificity for one or more sequences $S_T$ or $S_{AT}$.

It is quite particularly preferred In this case that the agent which stimulates the expression be specific for a sequence or several sequences $S_T$ or $S_{AT}$.

The above-described agent which stimulates the expression will be designated below as the expression stimulating agent ES.

An application in accordance with the invention of at least one of the agents in accordance with the invention for regeneration of tissue provides that the tissue to be regenerated is selected from the group which comprises degenerative tissue, traumatically damaged tissue, and tissue damaged by other means.

An application of at least one of the agents in accordance with the invention for the regeneration of tissue is particularly preferred if the tissue to be regenerated is mesenchymal tissue.

It is quite particularly preferred that the mesenchymal tissue be selected from the group which comprises cartilage, muscle, fat, and connective and support tissue.

A further application in accordance with the invention concerns the application of at least one of the agents in accordance with the invention for the regeneration of tissue in vivo.

The invention suggests that the use take place in humans and/or in animals.

Furthermore, the use for therapeutic application in humans and/or in animals is provided.

A further aspect of the invention concerns the use of at least one of the agents in accordance with the invention for regeneration of tissue in vitro.

It is particularly preferred that the application take place in or on cultures which are selected from the group which comprises cell cultures, tissue cultures, organ cultures, and combinations thereof.

In a further application in accordance with the invention, the agent in accordance with the invention is provided for the manufacture of a drug for therapeutic application in the regeneration of tissue.

In a further aspect, the invention concerns a kit for the regeneration of tissue which contains at least an agent $M_{MAKS}$ and/or an agent $M_{MAKP}$.

It is possible for a kit to contain at least one translation product of one or several of the sequences $S_T$ or $S_{AT}$ and/or of the corresponding transcript(s) which is present in native or mutant form and/or complete or fragmented and whereby said translation product(s) are present in native or mutant form and/or complete or fragmented and/or glycosylated, partially glycosylated, or not glycosylated and/or phosphorylated or not phosphorylated and/or chemically modified or not chemically modified.

In one embodiment at least one expression-stimulating agent ES is contained.

In a particularly preferred embodiment, it is provided that at least one agent $M_{MAKS}$ and/or at least one agent $M_{MAKP}$ and/or at least one translation product TP and/or at least one expression-stimulation agent ES is contained in the kit in accordance with the invention.

The kit can be used for therapeutic treatment and/or for diagnosis.

Furthermore, it can be provided that the kit is used in vivo.

It is provided that the kit is used for humans and/or for animals.

Finally, the kit can also be used in in vitro systems.

It is particularly preferred in this case if the kit is used in or on cultures which are selected from the group which comprises cell cultures, tissue cultures, organ cultures, and combinations of the same.

In a further aspect, the invention concerns a process for the regeneration of tissue in which at least one of the sequences $S_T$ or $S_{AT}$ is expressed in the tissue which is to be regenerated.

In a further aspect through which the object is attained, the invention concerns a procedure which comprises the following steps:
a) Preparation of cells which are designated target cells;
b) Introduction of at least one of the sequences $S_T$ or $S_{AT}$ into the target cells;
c) Induction of the expression by at least one of the sequences $S_T$ or $S_{AT}$ into the target cells; and optionally
d) Cultivation of the target cells.

It can be provided that in the cultivation of the target cells at least one of the sequence $S_T$ or $S_{AT}$ is expressed.

In a preferred embodiment, at least one of the sequences $S_T$ or $S_{AT}$ is introduced in vitro into the target cells by means of a procedure which is selected from the group which comprises transfection, microinjection, electroporation, gene transfer by means of liposomes, and transformation brought about through agents.

In addition, it can be provided that the expression and/or induction of the expression is influenced by at least one agent $M_{MAKS}$ and/or at least one agent $M_{MAKP}$ and/or at least one translation TP and/or at least one expressing-stimulating agent ES.

In one embodiment, the target cells can originate from an animal organism including from a human.

In another embodiment, it is provided that the target cells originate from an animal organism but not from a human.

It can be provided that the target cells represent a different cell type than the cell types contained in the tissue which is to be regenerated.

Alternatively, it can be provided that the cell types represent a cell type such as is contained in the tissue which is to be regenerated.

It is preferred that the target cells (de-)differentiate into pluripotent stem cells under the influence of at least one of the sequences $S_T$ or $S_{AT}$.

In a preferred embodiment of the procedure, the target cells are co-cultured with other cells and/or cell types.

It is particularly preferred In this case that the cells and/or cell types used for co-cultivation influence the differentiation state of the target cells.

In a further embodiment, the target cells are prepared through the withdrawal of material from an organism whereby the material is selected from the group which comprises biological fluids containing cells, individual cells, tissue, and organs.

It is furthermore provided that following introduction of at least one of the sequences $S_T$ or $S_{AT}$ in the target cells, these target cells are introduced into an animal organism.

It is further provided that following introduction of at least one of the sequences $S_T$ or $S_{AT}$ into the target cells, expression be induced in the target cells before the target cells are introduced into an animal organism.

In an alternative, following the introduction of at least one of the sequences $S_T$ or $S_{AT}$ into the target cells their expression is induced in the target cells after which the target cells were introduced into an animal organism.

In a preferred embodiment, the target cells which were introduced into an animal organism are in a differentiated and/or differentiation-competent condition.

In a quite particularly preferred embodiment, the animal organism is a human organism.

It is provided that the organism in which the target cells are introduced is identical with the organism from which the target cells were taken.

Alternatively, it is provided that the organism in which the target cells are introduced are different from the organism from which the target cells originate.

It can be provided that at least one of the sequences $S_T$ or $S_{AT}$ is introduced into the tissue in the organism which is to be regenerated and/or the corresponding cells.

In a particularly preferred embodiment, it is provided that at least one of the sequences $S_T$ or $S_{AT}$ is introduced into the tissue to be regenerated and/or the corresponding cells with the use of gene-therapeutic procedures.

In one embodiment of the procedure in accordance with the invention, the introduced sequence $S_T$ or $S_{AT}$ is expressed.

It is particularly preferred that the expression of the introduced sequence $S_T$ or $S_{AT}$ be influenced by at least one agent $M_{MAKS}$ and/or at least one agent $M_{MAKP}$ and/or at least one translation product TP and/or one expression-stimulating agent ES.

A particularly preferred embodiment in accordance with the invention provides that the tissue to be regenerated is selected from the group which comprises mesenchymal tissue.

A further quite particularly preferred embodiment of the procedure in accordance with the invention provides that the mesenchymal tissue is selected from the group which comprises cartilage, muscle, fat, and connective and support tissue.

In an additional aspect, the invention while achieving the object concerns the use of at least one of the sequences $S_{AT}$ in accordance with the invention for the treatment of tumor diseases.

In a further aspect in which the object is attained, the invention concerns the use of a MAG gene for the treatment of tumor diseases.

Another aspect of the invention in which the object is attained concerns the use of at least one high mobility group protein gene for the treatment of tumor diseases.

In a preferred embodiment, it is provided that the high mobility group protein gene is selected from the group which comprises the HMGI-C gene and the HMGI-Y gene.

The above genes or groups of genes are designated below as $G_G$.

It can be provided that sequences are used with essentially the same sequence of nucleic acids as the genes $G_G$.

In an alternative, sequences can be used with a sequence of nucleic acids which is, in essence, functionally the same as that of the genes $G_G$.

The above-defined sequences together with the above-defined genes $G_G$ will be designated below as sequences $S_G$.

In an additional embodiment, it is provided that the sequences $S_G$ have at least one sequence which codes for a DNA-binding portion of the corresponding translation product(s).

In an additional alternative of the invention, it is provided that the sequences $S_G$ in accordance with the invention and derivatives thereof have no sequence which codes for the protein-binding portion of the corresponding translation product(s).

Furthermore, it can be provided that the sequences $S_G$ or derivatives in accordance with the invention thereof have one or more sequences $S_r$ which replace or supplement that sequence or those sequences which code for the protein-binding portion of the corresponding translation product or products.

It is possible in this case for the sequence $S_r$ to be selected from the group which comprises other sequences of the human genome, sequences of other (donor) organisms, and artificial sequences and combinations thereof.

In one embodiment, it is provided that the sequences $S_{AT}$ and $S_G$, as well as derivatives thereof in accordance with the invention are present as a double strand and/or a coding and/or non-coding single strand and/or cDNA.

Furthermore, it can be provided that the sequences $S_{AT}$ and $S_G$ as well as derivatives thereof in accordance with the invention are present as natives and/or mutants and/or are fragmented or not fragmented.

In one embodiment of the invention, the sequences $S_{AT}$ and $S_G$ as well as derivatives thereof in accordance with the invention have at least one promoter and/or at least one enhancer element and/or at least one transcription termination element and/or at least one resistance gene and/or at least one other marking gene.

In one embodiment, at least one of the sequences $S_{AT}$ or $S_G$ or derivatives thereof in accordance with the invention are present as clones in a host system.

It is provided in this case that the sequences $S_{AT}$ and $S_G$ as well as derivatives thereof in accordance with the invention are present in at least one copy.

The above genes $G_G$, the sequences $S_G$, and the sequences or different embodiment forms derived therefrom will be designated below as sequences $S_T$.

According to the invention, the object is attained by an agent for treating tumor diseases that includes at least one $M_{SAT}$ agent selected from the group that includes sense DNA, sense RNA, sense cDNA, antisense DNA, antisense RNA and antisense cDNA, and combinations thereof, as a single strand and/or as a double strand, whereby the sequence of the $M_{SAT}$ agent corresponds to one or more of the $S_{AT}$ or $S_T$ sequences or to the corresponding transcript(s).

In a preferred form of embodiment it is provided that the sequence of the $S_{AT}$ or $S_T$ sequences or of the corresponding transcripts is present in native or mutant form and/or complete or as a fragment.

In a further form of embodiment it can be provided that the sequence of the $M_{SAT}$ agent is present in native or mutant form and/or complete or as a fragment and/or chemically modified or not chemically modified.

Furthermore the invention suggests an agent for treating tumor diseases that includes at least one $M_{PAT}$ agent selected from the group that includes polyclonal antibodies, monoclonal antibodies, and fragments and derivatives thereof, whereby the $M_{PAT}$ agent is acting against the $S_{AT}$ or $S_T$ sequence(s) and/or the corresponding transcript(s), which is(are) present in native or mutant form and/or complete or a fragment.

In the framework of the present invention, an agent for treating tumor diseases is moreover suggested that contains at least one $M_{PAT}$ agent selected from the group that includes polyclonal antibodies, monoclonal antibodies, and fragments and derivatives thereof, and whereby the $M_{PAT}$ agent is acting against one or more translation products of one or more of the $S_{AT}$ or $S_T$ sequences and/or of the corresponding transcript(s), which is(are) present in native or mutant form and/or complete or a fragment and whereby the said translation product or said translation products is(are) present in native or mutant form and/or complete or as a fragment and/or glycosylated or partially glycosylated or not glycosylated and/or phosphorylated or not phosphorylated.

The invention suggests a further agent for treating tumor diseases that is characterized by at least one translation product of one or more $S_{AT}$ or $S_T$ sequences and/or of the corresponding transcript(s), which is(are) present in native or mutant form and/or complete or as a fragment and whereby the said translation product(s) is(are) present in native or mutant form and/or complete or as a fragment and/or glycosylated or partially glycosylated or not glycosylated and/or phosphorylated or not phosphorylated and/or chemically modified or not chemically modified.

Finally the invention provides another agent for treating tumor diseases that includes at least one $M_{JAT}$ agent that is an expression inhibitor that has greater specificity for one or more of the $S_{AT}$ or $S_T$ sequences than for other tissues of the corresponding genetic system.

Furthermore the invention provides an agent for treating tumor diseases that includes at least one $M_{JAT}$ agent that is an expression inhibitor specific for at least one of the $S_{AT}$ or $S_T$ sequences.

In a preferred form of embodiment it is provided that the tumor to be treated expresses a gene selected from the group that includes MAG genes, high mobility group protein genes, HMGI-C genes, HMGI-Y genes, and their derivatives.

It can furthermore be provided that one of the agents of the invention is used to produce a drug for treating tumor diseases.

In a preferred form of embodiment it is provided that the drug is used for treating types of tumors that express a gene selected from the group that includes MAG genes, high mobility group protein genes, HMGI-C genes, HMGI-Y genes, and their derivatives.

In a further form of embodiment it can be provided that at least one agent of the invention is used for treating types of tumor that express a gene selected from the group that includes MAG genes, high mobility group protein genes, HMGI-C genes, HMGI-Y genes, and their derivatives.

A DNA sequence according to the invention, which is characterized by a sequence as shown in SEQ ID NOs: 1 to 19, is advantageous for developing novel agents based on this sequence and its corresponding transcripts and translation products, whereby the nucleic acids must be confirmed to be molecules carrying information in their structures. Such agents can be drug products, as well as agents used in diagnostics, but are not limited to these. These agents can also be used advantageously in various processes and also for the therapy of various illnesses or for producing appropriate drugs for treating these illnesses. Thus with the description of the sequences of the invention, a versatile agent is made available. It must be noted thereby that the advantages resulting from the sequences of the invention are not limited to an exact characterization of a specific site of action, which can therefore be affected by the use of suitable agents, including those of the invention, but the corresponding sequences themselves serve to cause effects based on the presence of the sequences of the invention or sequences derived therefrom and/or their transcripts and/or their translation products. These sequences can also be affected advantageously if they are biologically active as such in an organism, whether as a result of basic biological processes or as a result of the introduction of these sequences by means of a technical measure, or in an in vitro system.

These general advantages are also furnished if parts of the sequences shown in SEQ ID NOs: 1 to 19 are a part of the DNA sequence of the HMGI-C gene.

The term "genes" in connection with this application is intended to include the sequence of the exons and introns and also the corresponding cDNA of the respective gene.

Compared with the sequences shown in SEQ ID NOs: 1 to 19, mutations of the DNA sequence of the invention offer a further advantage in that they enable a sequence-specific agent, e.g. in the form of an antisense DNA acting against the sequences of the invention, to be distinguished from other sites of action if necessary, and thus the stringency occurring when nonmutant sequences are used would not guarantee the required specificity of interaction between the respective complementary strands.

Mutation in the sense of the present invention also includes a fragmentation of the sequences, whereby fragmentation includes shortening of the sequences at the 5'-end and/or at the 3'-end up to an oligomer, as well as loss of a sequence(s) of at least one nucleotide arranged within the sequence. Moreover the term "fragmented sequence or gene" herein is intended to include a sequence/gene that has one or more introns that can be respectively deleted partially or completely.

Furthermore, such mutant sequences allow translation products to be obtained whose biological activity is essentially identical to that of the translation products of native sequences. On the level of the amino acid sequence of the translation products, such mutations can manifest themselves in a variety of ways, including insertions, deletions, or silent mutations, among others. On the DNA level, such mutations allow the sequence to be matched to the use of certain tRNA anticodons and thus make it possible to match the translation rate of the corresponding sequences to the respective requirements or the respective host system.

On the other hand, applications are conceivable in which essentially the same sequence as the DNA sequence shown in SEQ ID NOs: 1 to 19 is advantageous and e.g. delivers the necessary stringency. A modified version of the DNA sequences of the invention also offers the possibility of including suitable signals recognized by the biological background. The presence of such signals can lead to a changed transcription and/or translation rate, e.g. as a result of an increased half-life of the transcripts, but is not limited to this.

The aforementioned advantages can also exist when nucleic acid sequences are used that are only functionally the same. It must be taken into consideration thereby that the term "functionally the same nucleic acids" takes into account the functional principle on which the HMGI-C gene, but also in general the MAG genes or the high mobility group protein genes, is based.

Without prejudice, there exists in the literature the perception that the corresponding gene products essentially consist of a DNA-binding portion and a protein-binding portion. As a result, this term "functionally the same nucleic acid sequence" is also intended to include those sequences that code for translation products with a similar function to the translation products of the sequences of the invention or of the MAG genes or of the high mobility group protein genes. The advantageous effects described above must also be taken into account for such translation products. The term is also intended to include those nucleic acid sequences that lead to a translation product that is functionally the same, i.e. those that lead to a functionally still active translation product in the above sense as a result of the degeneration of the genetic code. The fact that the sequences of the invention have a (nucleic acid) sequence that codes for a DNA-binding portion of the corresponding translation product(s), ensures that the sequences of the invention yield a translation product that is capable of binding to DNA. Vice versa, the nucleic acid sequence as such gives a precisely defined target for agents in which the required sequence specificity is inherent in their molecular structure, such as e.g. antisense DNA or antibodies acting against the DNA-binding portion of the sequence and/or of the corresponding translation products.

Because sequences of the invention sometimes lack a sequence that codes for the protein-binding moiety of the translation product(s) corresponding to the DNA sequences of the invention, there exists the possibility of influencing in a desired manner the effect on the chromatin structure that would otherwise be mediated via the protein-binding portion.

If on the other hand one or more $S_r$ sequences is(are) present that replace(s) or complete(s) the sequence(s) that code(s) for the protein-binding portion of the translation product(s) corresponding to the sequences of the invention, this opens up the advantageous possibility of a specific interaction with cellular (protein) components. As a result, other cellular factors can interact with the additional or new portions of the translation product. Vice versa, at the DNA level another region can thus be introduced that allows a response to the sequences of the invention.

Depending on the respective question under consideration, the sequence $S_r$, which is selected from the group that includes other sequences of the human genome, sequences of other (donor) organisms and artificial sequences and combinations thereof, also offers many possibilities for influencing cellular events.

The fact that the sequences shown in SEQ ID NOs: 1 to 19 are aberrant transcripts of the HMGI-C gene, makes it possible to distinguish between aberrant transcripts on the one hand, and non-aberrant transcripts on the other hand, and also between the respective translation products. For those skilled in the art, this results in a wealth of advantages in both the therapeutic and diagnostic fields.

Thus it is e.g. conceivable that the translation products of the aberrant transcripts stimulate or interrupt certain reaction chains in the cellular events, for example by acting as competitive inhibitors.

With an expression vector of the type according to the invention, which includes at least one transcription promoter followed downstream by at least one DNA sequence of the invention, there exists the possibility of obtaining corresponding transcripts and translation products of the DNA sequences of the invention in a simple and rapid manner.

Using a further form of embodiment of the expression vector, there is also the possibility of transforming or transfecting various host systems. Depending on the respective host system used, various promoters can be provided, both eukaryotic and prokaryotic, as well as optionally enhancer elements and/or suitable termination elements, as are sufficiently well-known in the state of the art.

Whether a prokaryotic or a eukaryotic cell is used as the host cell depends on the purpose for which the expression vector is being used. Owing to their nutrient requirements and comparatively greater ease of cultivation, prokaryotic cells are to be preferred when the inherent disadvantages of host systems of this type, such as e.g. lack of glycosylation or possibly the formation of inclusion bodies, are not important for the purpose of the cultivation.

On the other hand eukaryotic cells, especially yeast cells and mammalian cells, offer an advantage, e.g. when post-translational modifications are important for the further intended use.

Advantages are also gained from a protein or peptide that is a translation products[sic] of one or more $S_{AT}$ sequences and/or of the corresponding transcript(s) that is(are) present in native or mutant form and/or complete or as a fragment, and whereby the said translation product(s) is(are) present in native or mutant form and/or complete or as a fragment and/or glycosylated, partially glycosylated, or not glycosylated and/or phosphorylated or not phosphorylated and/or chemically modified or not chemically modified. Thus there exists the possibility of preparing effector molecules coded by the $S_T$ and/or $S_{AT}$ sequences, without changing the genetic background of the system under observation. In addition to direct substitution or completion of the cellular level with respect to the translation product(s) TP, e.g. in the form of "flooding," the possibility is also offered of influencing cellular events by using derivatives present in native or mutant form and/or complete or as a fragment, including the various possible glycosylation forms and the physiologically particularly important phosphorylation forms and other modified forms, whereby the said molecules can assist the effect of the native translation product if necessary, or else e.g. can also initiate this or can respond to the corresponding attachment sites of cellular mechanisms in the sense of a competitive inhibition.

The use of at least one sequence of the invention and/or of an MAG gene or at least a high mobility group protein gene and particularly the use of the HMGI-C gene or the HMGI-Y gene to influence vessel development is advantageous in that it gives a specific site of action as well as specificity of the agent to be used in principle to influence vessel development. This ensures that the expression of the corresponding genes or sequences is influenced by a suitable agent, which can include the corresponding genes or sequences themselves. Based on this very direct mechanism of action, all those disadvantages that occur with indirect mechanisms of action are avoided to a very great extent. This leads to less disturbance of the cellular processes in the sense of a nonspecific disturbance and thus in the end also to reduced secondary effects on the systemic level.

The explanations given above in connection with the advantageous effects of mutations and other forms of the $S_{AT}$ sequences of the invention also apply to the $S_T$ sequences of course, and are included herein for reference.

The advantageous effects are also furnished when the $S_T$ and/or $S_{AT}$ sequences are present as a double strand and/or a coding and/or noncoding single strand and/or cDNA. It lies within the framework of the present invention if the said sequences are present as DNA or as RNA. The use of such constructs according to the invention enables somatic and/or transitional gene therapy for influencing vessel development.

Furthermore it is advantageous if the corresponding sequences are also present as a single strand, whether coding or noncoding, whereby agents can then be used that act specifically on the single strand, in order to ensure that vessel development is influenced. It is possible for those skilled in the art to utilize the said sequences in both their native or mutant form and/or their fragmented form, without having to forego the advantage of the directly mediated action. Here too, the previous explanation concerning mutation and fragmentation applies.

Vessel development can also be influenced advantageously if the $S_T$ and $S_G$ sequences have at least one eukaryotic promoter and/or at least one enhancer element and/or at least one transcription termination element and/or at least one resistance gene and/or at least one other marker gene. The transcription and/or translation can be influenced by these elements in a way that is more advantageous for influencing vessel development. Thus a suitable eukaryotic promoter can be controlled, e.g. via the presence of specific factors and thus a predetermined expression can be induced by endogenous and/or exogenous factors. Resistance genes would allow further distinguishing of the cell populations to be influenced and could also be used as selection markers. A marker gene would be advantageous in this connection in so far as an indication of the processes proceeding at the molecular or molecular-genetic level could be ensured thereby.

Because the $S_T$ and/or $S_{AT}$ sequences are present as clones in a host system, there exists the possibility of achieving vessel development both in vivo and in vitro via the effects of the level of expression caused by the natural presence of the $S_T$ and/or $S_{AT}$ sequences. This can lead, for example, to particularly rapid vessel growth.

The fact that at least one copy, i.e. an $S_T$ and/or $S_{AT}$ sequence of the invention, is present in the respective biological system, makes it possible to achieve further advantageous effects in the sense of the above explanations, via gene dosage effects.

An agent of the invention for influencing vessel development selected from the group that includes sense DNA, sense RNA, sense cDNA, antisense DNA, antisense RNA, and antisense cDNA, and combinations thereof, as a single strand and/or a double strand, whereby this agent is(are)[sic] present in native or mutant form and/or complete or as a fragment and/or chemically modified or not chemically modified, is particularly advantageous.

If the sequence of the agent(s) corresponds to an $S_T$ or $S_{AT}$ sequence(s) or to the corresponding transcript(s), which is(are) present in native or mutant form and/or complete or as a fragment, it is possible to exert an influence via a corresponding interaction between the respective nucleic acids [text missing in original] the expression, i.e. the transcription and/or translation on the influencing of vessel development advantageously. Thus, it is e.g. conceivable to raise the level of expression of the corresponding sequences by using a suitable sense DNA or sense RNA. Vice versa, it is conceivable, e.g. in the case of reducing tumor angiogenesis, to use corresponding antisense DNA/antisense RNA and thus to reduce the expression. As a result of the reduced expression of the $S_T$ and/or $S_{AT}$ sequences, tumor angiogenesis is reduced, which leads to a reduction in the volume of the tumor until it disappears. Corresponding mechanisms are also obtained when cDNA or antisense cDNA are used. The advantageous effect can also be observed when the corresponding agent is present in non-native form, i.e. mutant and/or fragmented. Such mutations are advantageous in so far as the interaction of the sequence-specific agents with the $S_T$ and/or $S_{AT}$ sequences and/or cellular factors can be distinguished against the genetic background. Vice versa, a possibly advantageous response of original target sequences is possible with a sequence that is largely native. The corresponding sequences of the agents used do not necessarily have to be present in complete form, i.e. in complete length; favorable effects can also be achieved when they are present as a fragment, as defined above.

It is also conceivable for the agent of the invention to be introduced into the cell or be present there and itself serve as a matrix, and for it to have biological effects. Such effects can be caused by DNA and/or RNA and/or corresponding translation products. Thus the possibility of somatic gene therapy and/or transitional gene therapy is opened up by the agents of the invention.

Although the use of both DNA and RNA is possible in principle within the framework of the agents of the invention, owing to the reduced stability of RNA in biological systems, the use of DNA may be appropriate when a longer-term effect is desired, and vice versa the use of RNA may be appropriate when only a short-term influence on the corresponding sequences is desired.

Chemical modification of the agents of the invention may be advantageous among other things in so far as e.g. the biological half-life of the agent can be influenced thereby and thus the duration of the action of the agent of the invention can be influenced precisely.

There are quite particular advantages when the corresponding agent is acting against the $S_T$ and/or $S_{AT}$ transcripts. Thus the accessibility of the transcripts relative to the sequences typically present as a double strand can be important for the effectiveness of the inhibition, but also for the effectiveness of the stimulation. In addition to the native form, the mutant form of the transcript also offers the possibility of a further influencing of the specificity of the interaction, whereby the corresponding transcripts can optionally be present complete or as a fragment, whereby the various splice forms are to be understood as a fragment in addition to the forms defined above.

With an agent of the invention for influencing vessel development selected from the group that includes polyclonal antibodies, monoclonal antibodies, and fragments and derivatives of the same, a specific tool is made available for advantageous use. The specificity of said agent is acting against the $S_T$ and/or $S_{AT}$ sequences and/or the corresponding transcript(s), which is(are) present in native or mutant form and/or complete or as a fragment. Thus the aforementioned specificity of the agent causes a highly specific interaction with said sequences. In addition to the epitopes established by the native sequences, including those yielded by the respective transcription products, the mutant transcription products of the optionally mutant sequences are also tissue- and organ-specific compared with the remaining cellular antigenic background, or that of other cells, so that the target cell specificity of optionally systemically applied agents required for influencing vessel development—associated with the fewest possible side effects—is ensured. The same also applies to the presence of fragments of the transcription products.

In addition to the use of polyclonal and monoclonal antibodies, the use of fragments and derivatives thereof can also be particularly advantageous in the sense of the present invention. Fragments include all those forms of molecules derived from antibodies that continue to allow more or less specific binding to an antigen or epitope. Derivatives are understood to mean antibodies or fragments derived from the original structure of the antibodies. These include, among others, antibodies comprising only one protein chain, as well as marked antibodies. Markings include all those described in the literature and include among others marking with enzymes, luminescence, complex-formers, biotin and biotin derivatives, digoxigenin, and radioactive markers.

It is furthermore provided that the antibodies, fragments, and derivatives of these are modified so that uptake into the cell is possible utilizing biological and/or chemical and/or physical mechanisms. Such a modification can consist for example in that the molecule has at its disposal an additional structure (e.g. a corresponding domain or attached compound) that enables receptor-mediated or other, possibly non-specific, uptake.

What has been explained above with respect to the specificity of the said agent opposite to $S_T$ and/or $S_{AT}$ sequences or the corresponding transcripts also applies to their translation products. Here too, in addition to the [text missing in original] by the native form of the translation products of the sequences or their transcripts, those translation products are particularly important that are translated from mutant sequences. In addition to the numerous epitopes of the native translation products present, the aberrant translation products are of particular interest for a selective response by defined cell populations, whereby in addition to the disappearance of epitopes previously present, the new appearance of epitopes is also of importance. Such epitopes can in principle be caused both by the primary sequence and also by the secondary, tertiary, or quaternary structure, and can also affect the glycosylation and phosphorylation sites.

The specificity of an agent for influencing vessel development can also be influenced by an agent that is itself selected from the group, including polyclonal antibodies, monoclonal antibodies, and fragments and derivatives of these, in that this agent is acting against the antibodies or fragments or derivatives, which for their part are acting against the $S_T$ and/or $S_{AT}$ sequences and/or the corresponding transcript(s) in their various forms, as defined above, or opposite to the corresponding translation product(s) in their various forms.

An advantageous influencing of vessel development is also allowed by an agent of the invention for influencing vessel development that [word missing in original] at least one translation products[sic] of one or more $S_T$ and/or $S_{AT}$ sequences and/or of the corresponding transcript(s) that is(are) present in native or mutant form and/or complete or as a fragment, and whereby the said translation product(s) is(are) present in native or mutant form and/or complete or as a fragment and/or glycosylated, partially glycosylated, or not glycosylated and/or phosphorylated or not phosphorylated and/or chemically modified or not chemically modified.

The said advantages of a protein or peptide that is a translation product of one or more S[sub]AT sequences and/or of the corresponding transcript(s), which is present in native or mutant form and/or complete or as a fragment, also apply of course to the agent of the invention and are herewith included for reference.

Other advantages result from the use of at least one expression inhibitor and/or at least one expression-stimulating agent in the framework of an agent for influencing vessel development. The aforementioned $M_{MAKS}$ and $M_{MAKP}$ agents of the invention can also represent such expression inhibitors or expression-stimulating agents. Expression inhibitors and expression-stimulating agents different from these are also included, however. It is within the meaning of this invention that the genetic background is modulated relative to the expression of $S_T$ and/or $S_{AT}$ sequences by corresponding inhibitors or stimulating agents. The desired influencing of vessel development can result from this relative relationship of the expression of the genetic background on the one hand and of the $S_T$ and/or $S_{AT}$ sequences on the other hand. It is also entirely possible to use said $M_{MAKS}$ and $M_{MAKP}$ agents in addition to the—nonspecific, since they influence the total genetic background of the cellular system—inhibitors and/or stimulating agents.

The selectivity of the influencing of vessel development can be increased in an advantageous manner with an increased specificity of the expression inhibitor or the expression-stimulating agent for one or more of the $S_T$ and/or $S_{AT}$ sequences, compared with other genes of the genetic system concerned.

The said advantages concerning the influencing of vessel development also extend to angiogenesis, whereby this can if necessary be reduced and/or interrupted in an advantageous manner. Vice versa, stimulation of angiogenesis is also possible and can be carried out advantageously using the $S_T$ and/or $S_{AT}$ sequences in the broadest sense, including the corresponding translation products and the agents of the invention.

The agent of the invention is of central importance for influencing vessel development when this relates to tumor angiogenesis. As already explained, the presence of a vascular system is essential for the growth of a tumor. With the sequences and agents of the invention or the use of the invention of the $S_T$ sequences in the broadest sense and including the translation products and the agents derived therefrom, it is now possible to control tumor angiogenesis and thus a novel method is set forth for the treatment of various tumors. Thus comparatively nonspecific therapies such as chemo- and radiation therapy with their widely known side effects become obsolete, and instead a highly specific form of therapy is made possible. A further impairment of systemic angiogenesis can also be avoided by suitable measures, such as e.g. administration of the agent explicitly at the site of the tumor angiogenesis.

Said specificity is based among other things on the fact that stronger expression of HMGI-C has not been found hitherto in any tissue of the adult organism, with the exception of the endometrium, so that in fact the development of blood vessels in the environment of the tumor can be interrupted selectively.

The explanations given in connection with angiogenesis also apply when the agents or their use relate to influencing vessel development in the sense of vascularization.

Just as in other diseases, processes of (neo-)angiogenesis, (neo-)vascularization, and disturbances of vascularization also play a large part in vision impairments such as e.g. in diabetes mellitus. Thus an advantageous specific treatment is possible here too, using the agents or sequences of the invention, as is surmounting the initially explained disadvantages of existing therapies. The preventive aspect of such a treatment is of considerable importance when the agents or sequences of the invention are used according to the invention, so that further impairment of the health and well-being of the patient by a vision impairment is avoided.

The use according to the invention of the agents of the invention for influencing vessel development can be used advantageously in improving the blood supply of infarct-damaged heart muscle tissue. (Neo-)angiogenesis and (neo-)vascularization enable the heart muscle tissue to be better supplied with vessels thereby. In addition to achieving a fundamentally improved state of health of infarct patients, either bypass operations can be omitted completely or the healing process can be successfully reinforced. Moreover the use according to the invention relates to improved blood supply to the heart muscle tissue in general and to that of high-risk patients specifically.

The advantages with respect to influencing vessel development extend to both the human and animal organism, whereby a therapeutic and/or diagnostic use is advantageous in humans and/or animals.

In addition to the direct benefit that a human experiences by the influencing of vessel development, whether for regeneration purposes or for the treatment of tumor diseases or effects of diabetes mellitus (impairment of vision), the benefit can also be of an indirect nature, e.g. when appropriate vessel material is produced for transplantation purposes, under the influence of the sequences and/or agents of the invention or uses in animals.

Use in the sense of veterinary medical use is also included, of course.

In addition to this very broad therapeutic use, an advantageous diagnostic use is also possible in principle in both humans and animals. It is particularly advantageous thereby to use the $M_{MAKS}$ and $M_{MAKP}$ agents, above all when they carry markers that can be detected by means of non-invasive test methods. Thus, for example, it can be checked whether a therapeutic measure has the desired success at the genetic level. Influencing vessel development according to the invention is also advantageous when an agent of the invention and/or one of the $S_T$ and/or $S_{AT}$ sequences or their uses is(are) used in vitro. This includes use in cell, tissue, and organ cultures, among others.

Finally, the agent of the invention or its use can also be used to produce a drug for therapeutic and/or diagnostic use, so that a drug is available that is clearly superior to agents of the state of the art used for the purpose of influencing vessel development or for the purpose of treatment of diabetes mellitus and tumor diseases, as far as side effects associated with these are concerned.

The aforementioned advantages also apply of course to the kit of the invention in its various forms of embodiment and are included herein for reference. The same applies to the advantages resulting from the individual components of the kit.

The advantages of a kit are generally considered to be in that, among other things, the respective agent is ready prepared in the optimal manner for its use. This also includes a suitable spatial arrangement. Advantageous effects can result thereby precisely from the combination of the various agents.

In addition to its therapeutic use for influencing vessel development, including reduction of tumor angiogenesis for treating effects of diabetes mellitus and for improving vessel provision of infarct-damaged heart muscle tissue, the kit of the invention can also be used for diagnostic and test purposes; e.g. information can be gained advantageously as to how far certain therapeutic measures are characterized by success or whether certain substances produce the effects ascribed to them.

The explanations given in connection with the use of the $S_T$ and/or $S_{AT}$ sequences of the invention in the broadest sense, including the corresponding transcripts and translation products, as well as in connection with the agents of the invention for influencing vessel development, of course apply also to their use for treating endometriosis and to corresponding agents and kits of the invention for treating endometriosis and are included herein for reference.

Without prejudice, it is assumed that the structuring of the endometrium takes place under the influence of the expression of the HMGI-C gene, even when endometriosis is present, as a result of which influencing the expression of this gene or functionally similar genes by using the said sequences or agents and kits leads to a specific treatment for endometriosis that is virtually free of side effects.

The explanations given in connection with the use of the $S_T$ and/or $S_{AT}$ sequences of the invention in the broadest sense, including the corresponding transcripts and translation products, as well as in connection with the agents of the invention for influencing vessel development, of course apply also to their use for contraception and to corresponding agents and kits of the invention and are included herein for reference.

Here too the invention is based on the surprising finding that the HMGI-C gene participates in the structuring of the endometrium. When the sequences or agents of the invention are used, contraception or pregnancy is achieved by specifically influencing the endometrium receiving the fertilized ovum, for example in the sense of suppressing its structuring. Since the HMGI-C gene is expressed almost exclusively in the endometrium in the healthy adult human organism, this ensures that even when an appropriate agent is applied systemically, only the desired target site, i.e. the endometrium, is exposed to the influence of the corresponding agents of the invention and thus the side effects observed when hormonal agents are administered for contraception are virtually absent.

The uses according to the invention or agents and methods for contraception provide for local contraception as well as oral contraception. In addition to the significant advantage of decidedly simple and reliable oral administration in the framework of oral contraception, local contraception also offers advantages. Thus the formulation of the appropriate preparations can be simple, since gastrointestinal passage is not necessary. Instead, it can be ensured by means of e.g. aerosols that the agents of the invention reach their site of action, i.e. the endometrium, directly.

Further advantages resulting from the individual forms of embodiment of the use of the invention, like those resulting from the agents of the invention for contraception and the methods of the invention for contraception, have of course already been stated in connection with the influencing of vessel development and are included herein for reference.

As far as advantageous effects are concerned, it can also be stated that by periodic administration of the agent of the invention or by means of the processes of the invention, a cyclicity becomes possible with respect to the structuring of the endometrium that may be useful from the point of view of basic medical or biological considerations and represents a therapeutic use of the agents of the invention, for example in cases of menstrual problems.

An advantage of the process of the invention that should be particularly emphasized is that the agents of the invention can be administered after conception. Without prejudice as to the mechanism of action, it can be stated that according to our present understanding, the structuring of the endometrium can be influenced before, during, and after nidation by influencing the expression of the HMGI-C gene or analogous genes, so that the endometrium degenerates and the pregnancy is interrupted.

The explanations given in connection with the use of the sequences of the invention and $S_T$ sequences in the broadest sense, including the corresponding transcripts and translation products, as well as in connection with the agents, kits, and optionally processes of the invention for influencing vessel development and for contraception, of course apply to their use for tissue regeneration and to corresponding agents, kits, and methods of the invention, and are included herein for reference.

Tissue regeneration is understood herein to mean both regeneration of tissue with recourse to exactly the type of tissue to be regenerated, in the sense of an increase in the mass of the tissue, as well as the production of new tissue starting from a different type of tissue or cell than that to be produced.

Furthermore the uses, agents, kits, and processes of the invention for tissue regeneration allow the regeneration of tissue that hitherto could not be regenerated or only with difficulty, or makes corresponding regeneration processes safer overall both for the personnel entrusted with the task of tissue regeneration and for the final recipient of the tissue regenerated in this manner; through the use of the invention and the kit of the invention and the process of the invention, however, defined conditions are created that allow a specific intervention in the sequence of events of tissue regeneration, while avoiding the involvement of material from biological sources that pose a risk, at least latent, in the form of possible viral (hepatitis C, HIV) and bacterial contamination, as well as factors not tolerated immunologically (anaphylactic shock).

The use of at least one of the agents of the invention in vivo is associated with considerable advantages for a number of reasons. Thus for example no collection of material is required from any tissue or organism whatsoever. Thus rejection reactions resulting from tissue incompatibility and problems that might result from the use of material from biological sources do not occur.

Vice versa, the use of at least one of the agents of the invention in vitro can likewise be advantageous, namely when a corresponding use is not possible under the conditions currently prevailing in the organism. This may be the case e.g. when no tissue is available in principle that is suitable to serve as starting material for the regeneration process of the invention. The use in or on cultures selected from the group that includes cell cultures, tissue cultures, organ cultures, and combinations thereof, facilitates controlled tissue regeneration to a not inconsiderable extent, while the uses of the invention or agents and processes used for this purpose can be used and carried out under defined conditions. Moreover there exists the possibility in such in vitro systems of producing corresponding material beyond the respective current need and thus of being in a position to satisfy an unforeseen need.

In connection with this application, a therapeutic treatment is also intended to include such a treatment for cosmetic purposes.

It is moreover held that the use of an agent of the invention is quite particularly advantageous in the process of the invention.

For the process of tissue regeneration, a variant can also be advantageous from the point of view of cost-effectiveness of the process or safety, in which the prepared or cultivated target cells already express at least one of the $S_T$ and/or $S_{AT}$ sequences, whereby the process step of the invention would omit the introduction of at least one of said sequences. The subsequent steps of the process remain unchanged.

Depending on the tissue to be regenerated, various processes can be selected to introduce the $S_T$ and/or $S_{AT}$ sequences. Those skilled in the art can ascertain the optimal transformation- or transfection protocol in each case by appropriate routine tests.

Target cells originating from a human are quite particularly advantageous. The human concerned can be the person who is to receive the tissue regenerated according to the invention, or else another person who is a suitable donor. In principle, target cells from a dead person can also be used. The latter may be the case, e.g. if no suitable living donor is available, or if a suitable donor is already dead and his tissue, for example because of age, is no longer suitable for direct transplantation purposes.

It can also be advantageous, however, if target cells originate from an animal organism other than a human. Thus, e.g., the use of target cells that originate for example from a transgenic animal may make sense under certain conditions, particularly if the transgenic animal yields target cells that are histocompatible with those of the recipient organism or have other advantageous properties.

The use of target cells that represent a different type of cell from the cell types contained in the tissue to be regenerated is advantageous when target cells taken from the tissue to be regenerated are not suitable for regeneration purposes. Using the process of the invention, corresponding agents, and kits, such target cells can be caused to regenerate in the sense of a proliferation and differentiation.

Vice versa, the use of target cells that belong to the same cell type as that contained in the tissue to be regenerated can increase the success of the process, above all when the tissue to be regenerated is still sufficiently intact, but the extent of the tissue still present is not enough to fulfill the respective biological function to its full extent.

The (de-)differentiation of the target cells under the influence of at least one of the $S_T$ and/or $S_{AT}$ sequences of the invention in the broadest sense, including of the corresponding transcripts and translation products, as well as agents of the invention acting against these, to produce pluripotent stem cells, allows cells to be changed into a condition that allows development of the respective cell into each mesenchymal cell type and thus allows the regeneration of almost any desired mesenchymal tissue. This also includes a case in which the direction in which the regeneration of the invention finally proceeds, is determined by the influence of additional factors, if necessary of the cellular environment in which the cell is situated or into which the cell is introduced.

Advantageous effects occur when target cells of the process of the invention are co-cultivated with other cells and/or cell types. As already indicated in the above section, co-cultivation can have a determinative influence on the direction of the (re-)differentiation of the target cells in the sense of a tissue regeneration. Without prejudice, it can be assumed that influences apparently emanate from the cells used for the co-cultivation that influence the differentiation state of the target cells. Such an influence can be mediated by more or less soluble factors, but also cellularly, with the latter also including interactions of cell membrane structures or components in the broader sense as well as other physical or chemical phenomena such as e.g. membrane potentials.

Depending on the type of tissue to be regenerated, as well as on the sources available in principle, the material collected from an organism can be selected from the group that includes cell-containing biological fluids, cells, single cells, tissue, and organs. With the collection of cell-containing biological fluids or single cells, it is ensured that further steps to recover single cells from tissues or organs are avoided to a great extent. This ensures that cells are utilized for regeneration purposes that actually appear to be best suited for the respective case. It can also be advantageous, however, to collect tissue or even complete organs. Thus it is conceivable that with the collection of tissue or organs, several cell types are available whose suitability can be tested during a routine test processing. Moreover when tissues or organs are collected, an advantage can result in that otherwise the collection of suitable cell material would be impossible.

After introduction of at least one of the $S_T$ and/or $S_{AT}$ sequences of the invention, the introduction of target cells into an animal organism offers advantages in that the respective animal organism, including the human, thus contains biologically active tissue in order to eliminate defects or deficiencies relating to this. The target cells can be introduced thereby when the target cells are either in the form of single cells, or, after cultivation, are already in the form of cell aggregates, tissue, or the like. Finally it is also conceivable in principle for the target cells to be introduced into an animal organism in order to develop there further under the influence of the biological system. Later collection of the target cells further modified and/or increased and/or differentiated in the biological system, i.e. the animal organism, is likewise to be included thereby.

After introduction of at least one of the $S_T$ and/or $S_{AT}$ sequences of the invention into the target cells, it can be advantageous to induce their expression in the target cells before the target cells are introduced into an animal organism. The advantage is that thus the possible influence of the biological system on the differentiation is limited. This can be particularly advantageous when differentiation of the target cells in the desired direction would not be guaranteed in a cellular environment owing to the differentiation factors or signals there.

Vice versa, it is also advantageous, after introduction of at least one of the sequences of the invention or $S_T$ sequences, to induce their expression in the target cells after the target cells have been introduced into an animal organism. This subsequent induction can be advantageous if the proliferation and/or differentiation of the target cells is only to take place under the influence of the target region or the target tissue with its specific differentiation signals and factors, in order to exclude premature differentiation in a direction other than the desired one.

Of course, the said advantages also result with respect to whether the target cells introduced into an animal organism are in a differentiated and/or differentiation-competent state.

If the animal organism into which the target cells are introduced is a human organism, particular advantages result therefrom, among others with respect to the treatment of degenerative diseases, such as e.g. arthritic diseases or muscular dystrophy. Similar to the advantages discussed in connection with the recovery of suitable target cells, these also result from the fact that the target cells are introduced into an organism that is identical with the organism from which the target cells were collected.

Vice versa, it can also be advisable for the organism into which the target cells are introduced to be different from the organism from which the target cells originate, e.g. when the organism into which the target cells are introduced no longer has any of its own starting material available.

Quite particular advantages result in the processes of the invention when at least one of the $S_{AT}$ sequences of the invention or the $S_T$ sequence is introduced into the tissue in the organism that is to be regenerated and/or the corresponding cells. Such a measure ensures that no surgical operations are required, either for collection or reintroduction of corresponding material, which is of central importance when the regions from which the material is collected or into which the material is introduced are only accessible by invasive means. Moreover the work required is reduced, as is the risk that the tissue to be regenerated is contaminated or else that a non-optimal regenerative development occurs under the conditions of in vitro cultivation.

Introduction of the constructs concerned as such into the tissue to be regenerated and/or the corresponding cells using gene therapy processes presents a quite particularly advantageous possibility, with particular advantages resulting from the use of suitable viral systems. Using routine tests for the application concerned, those skilled in the art can ascertain the process required for introduction of the sequences.

Finally, other advantages also result from the fact that expression of the introduced sequences of the invention and the $S_T$ sequences is influenced by at least one $M_{MAKS}$ agent and/or at least one $M_{MAKP}$ agent and/or at least one translation product TP and/or at least one expression-stimulating agent ES. Thus there exists the possibility of controlling the extent of the regeneration both with respect to its spatial pattern and also with respect to its time course.

The uses and agents of the invention for treating tumor diseases are generally advantageous in so far as a specific therapy for tumor diseases thus becomes possible, without the occurrence of systemic side effects as is the case with other therapies for treating tumor diseases such as e.g. chemotherapy or radiation therapy. As already stated, only a few tissues in the healthy organism express the $S_{AT}$ or $S_T$ sequences of the invention, whereas they are expressed strongly in a number of tumor diseases. As a result the agents, kits, and processes of the invention, which are specific for said sequences, allow a specific therapy for cancer, which moreover is free of side effects as a result of the mechanism of action on which it is based.

Although not limited to these, quite particular advantages with respect to specificity and reduction of side effects, as well as efficacy of the agent of the invention, result when the tumor to be treated expresses a gene selected from the group that includes MAG genes, high mobility group protein genes, HMGI-C proteins, HMGI-Y genes, and their derivatives. The same applies to the use of at least one of the agents of the invention for producing a drug for treating tumor diseases.

Further advantages of the various forms of embodiment of the agents of the invention and kits that contain these individually or in any combination for treating tumor diseases, as well as of the uses of the invention, result of course from the explanations in association with the uses of the invention of the $S_T$ and $S_{AT}$ sequences of the invention in the broadest sense, including the corresponding transcripts and translation products, agents and kits and optionally processes for influencing vessel development, for contraception, and for tissue regeneration, and are included herewith for reference.

The DNA sequences claimed in the invention are shown as SEQ ID NOs: 1 to 19. When the bases given in SEQ ID NOs: 1 to 19 are other than A, C, G, and T, the following nomenclature applies:

R can be A or G,
Y can be C or T,
K can be G or T,
M can be A or C,
S can be G or C, and
W can be A or T.

For further illustration of the invention, eight Examples are also given below, chosen at random from the wealth of material available.

The techniques used in the following Examples are summarized below. When changes are required for the individual Example, they are stated at the appropriate points.

Reverse Transcriptase Polymerase Chain Reaction (RT-PCR)

The reverse transcriptase polymerase chain reaction (RT-PCR) includes the transcription of RNA into cDNA which is then subjected to a regular polymerase chain reaction using a suitable primer.

In the examples described herein, the RNA was isolated with the TRIzol reagent (Life Technologies, Gaithersburg, U.S.A.). The tissues, healthy tissue as well as tumor tissue, were stored under liquid nitrogen for the time between removal/operation and start of the RNA isolation.

The RNA was transcribed into cDNA using the M-MLV Reverse Transcriptase (Life Technologies, Gaithersburg, U.S.A.), and then used for the RT-PCR.

The RT-PCR was conducted as a so-called nested PCR, that is, as a sequence of two polymerase chain reactions with the primers used being nested into each other. As a special case, in the polymerase chain reaction employed herein the primers were nested on one side only, on the other side the same primers were used for both polymerase chain reactions. FIG. 1 shows details and the position of the primers within the exon of the HMGI-C. The PCR shown in FIG. 1 does not cover shortened or aberrant transcripts missing the exons 4 and 5. Therefore, in addition to the PCR with the primers shown above, in some cases a PCR was used where the primer Revex 4 (see FIG. 1) was replaced by a primer from the $3^{rd}$ exon. The procedure used for the rapid amplification of 3' cDNA ends (3' RACE PCR, rapid amplification of cDNA ends) was as described by Schoenmakers et al., in Nature Genet 10:436 (1995). The sequences of all used primers are summarized in Table 1.

TABLE 1

Primers used for the RT-PCR of the HMGI-C, their sequences (each from 5' to 3') and their positions within the gene

| Primer name | Sequence | Position |
|---|---|---|
| SE1 | CTTCAGCCCAGGGACAAC (SEQ ID NO:20) | Exon 1 |
| P1 | CGCCTCAGAAGAGAGGAC (SEQ ID NO:21) | Exon 1 |
| Revex 3 | TTCCTAGGCCTGCCTCTT (SEQ ID NO:22) | Exon 3 |
| Revex 4 | TCCTCCTGAGCAGGCTTC (SEQ ID NO:23) | Exon 4/Exon 5 |

Cytogenetic and Molecular Cytogenetic Procedures

The cytogenetic and molecular cytogenetic procedures (fluorescence in-situ hybridization) were performed according to published standard methods (Bullerdiek et al., Cytogenet Cell Genet 45:187 (1987); Kievits et al., Cytogenet Cell Genet 53:134 (1990)). The following probes were used: cRM133, cRM76, cRM99, cRM53 (Schoenmakers et al., Nature Genet 10:436 (1995)).

Example 1

Expression of the HMGI-C Gene in Normal Tissue

Different tissue types were investigated with RT-PCR with regard to the expression of the HMGI-C gene; only tissues of non-tumor source were tested.

The results are summarized in Table 2.

TABLE 2

Tissues tested for expression of the HMGI-C gene, its origin (epithelial/mesenchymal) and extent of the expression of the HMGI-C gene

| Tissue | Origin | HMGI-C Gene |
|---|---|---|
| Myometrium, smooth muscles | mesenchymal | – |
| Adipose tissue, hypodermis and Endometrium | mesenchymal epithelial/mesenchymal | – ++ |
| Umbilical cord | mesenchymal | – |
| Blood vessels (adult) | mesenchymal | (+) |
| Blood vessels (fetal) | mesenchymal | ++ |
| Skin (fetal, gestation week 11) | epithelial/mesenchymal | ++ |
| Cartilage | mesenchymal | – |
| Cartilage (fetal, gestation week 11) | mesenchymal | ++ |

++: strong expression
+: weak expression
(+): very weak expression
–: no detectable expression From among the tested normal tissues, adult blood vessels showed a very weak and fetal blood vessels (arteria and vena umbilicalis) a significantly stronger expression of the HMGI-C gene. Endometrial tissue of the proliferation phase and the fetal tissues also showed a marked expression. All other tissues showed no expression.

The tests were conducted with the gene of the HMGI-C as a model; based on the extensive sequence homology and the similar expression patterns in the embryonal and fetal development of the mouse, similar results can be expected with the HMGI-Y gene.

Example 2

Aberrant Transcripts of the HMGI-C Gene cDNA was isolated from established cell lines and primary tumor material from human benign mesenchymal tumors (uterus leiomyoma, pulmonary hamartochondromas, aggressive angiomyxoma) as well as from tumors of the head salivary glands; it was then amplified by RACE-PCR and sequenced.

The obtained sequences are compared to sequence of the native HMGI-C gene.

Based on the results of this sequencing, a transcript or its cDNA was labeled as an aberrant transcript when, as a minimum, the sequence of the exons 1-3 (of a total of 5 exons) is present, and the sequence of exon 3 is followed by a sequence other than that of exon 4 or the sequence of exon 4 is followed by a sequence other than that of exon 5. The sequences fused to the HMGI-C gene were regarded as ectopic when their origin from a region of the chromosome 12 other than that of the HMGI-C or from another chromosome could be verified.

The tests performed as described yielded various aberrant transcripts detailed in SEQ ID NOs: 1-19. The sequence of the transcripts always starts with the $1_{st}$ nucleotide of exon 1 of the HMGI-C gene; the region of the sequence between the first nucleotide of the first exon and the first nucleotide of the primer was added from a databank. The sequence contains either the complete sequence to the poly-A tail or a part thereof. In any case, the sequence goes far beyond the $3^{rd}$ exon or $4^{th}$ exon and therefore characterizes the aberrant transcript.

Example 3

Rearrangement of the HMGI-C Gene in Hemangiopericytomas

Tumor material from two tumors, fixed in a paraffin matrix, was subjected to a fluorescence in-situ hybridization. Cosmid clones obtained from the region of the HMGI-C or the sequences directly flanking on 3' and 5' were used as probes. The tests were performed on interface nuclei isolated from the tumor material and showed the breaking points to be within the cosmid covered regions of the tumors tested; this allowed for the conclusion that this is the same type of mutation as with the other mesenchymal tumors.

Example 4

Differentiation of Cells with Mutant HMGI-C Gene

Cells of tumors with verified rearrangement of the HMGI-C gene (3 lipomas, 5 pulmonary hamartomas, 2 uterus leiomyomas) were co-cultured with normal cartilage cells. The cell culture conditions (Bullerdiek et al., *Cytogenet Cell Genet* 45:187 (1987)) for the co-cultivation were adjusted such that in the culture the differentiated status of the cartilage cells was maintained (no addition of fetal calf serum). The tumor cells originated from primary cultures with additional fetal calf serum. In the cell culture the tumor cells differentiated into cartilage cells, independent of whether they were tumors containing cartilage or not.

Example 5

Inhibition of Neoangiogenesis and Neovascularisation

Events related to neoangiogenesis, neovascularisation and vascularization defects are important factors not only in the development of tumors but also in the pathogenesis of many other diseases such as diabetes mellitus (Battegay et al., J. Mol. Med. 1995 (73), 333-346). The example described herein examined the role of the HMGI-C gene with regard to neoangiogenesis and neovascularisation using the techniques described at the beginning and including clonality tests (Noguchi et al., *Cancer Res.* 52:6594 (1992)). The techniques mentioned at the beginning and the clonality tests showed that the observed vascularization originated from the tumor cells themselves. Because of the role of HMGI-C in the proliferation and differentiation of pericytes, the neovascularisation of myomas, lipomas, leiomyomas and aggressive angiomyxomas originating from the tumor cells, and based on the data to the gene expression, the (neo)angiogenesis and the (neo)vascularization can be affected as desired by the sequences shown in SEQ ID NOs: 1-19, the sequences $S_T$, the claimed means and materials, kits and possibly methods, or by their use.

Example 6

Treatment of Endometriosis

The term endometriosis refers to ectopic endometrium that participates "in the normal cyclical and the pathological changes of the endometrium corporis" (Psychrembel, 1982). The histologic structure conforms to the normal endometrium in so far as epithelial and mesenchymal components are present. It could be shown, using the techniques described at the beginning, that the organization of the ectopic endometrium is based on the expression of the HMGI-C gene, similar to physiologically normal endometrium. Therefore, treatment of endometriosis can be based on the sequences shown in SEQ ID NOs: 1-19, the sequences $S_T$, the claimed means and materials, or their use.

Example 7

Contraception

Using the techniques described at the beginning it could be shown that the expression of the HMGI-C gene is involved in the organization of the endometrium. Thus, the sequences shown in SEQ ID NOs: 1-19, the sequences $S_T$, the claimed means and materials or their use provide means and methods for contraception.

Example 8

Chromosomal Breakpoint

Using the techniques described at the beginning, three pulmonary hamartochondromas were investigated, all of which showed a translocation between chromosome 12 and 14 with presence of two normal chromosomes 12 and one derivative 14, with the corresponding derivative 12 missing. The chromosomal breaking point on chromosome 12 was situated 5' from HMGI-C, the expression of which was also shown in all tumors.

This proves that incorporating one of the sequences $S_T$ or $S_{AT}$ leads to a proliferation of normal tissue which can be used for purposes of tissue regeneration or stimulation of angiogenesis or vascularization.

Example 9

Expression of the HMGI-C Gene Upon Cartilage Formation During Embryonal Development of the Mouse A cDNA fragment of the HMGI-C gene of the mouse (approx. 1.8 kb length, approx. 800 bp 5' UTR to 200 bp 3' UTR) was cloned into an in-vitro translation vector. The presence of T7 or Sp6 RNA polymerase promoters was exploited to synthesize a RNA probe suitable for in-situ RNA-RNA hybridization. This probe was then used for hybridizing in tissue slices of mouse embryos in different stages of development. The results show that, among others, a very strong expression of the gene occurs during cartilage formation from mesenchymal progenitor cells.

This expression is not only detected with mesenchyma of mesodermal but also of ectodermal origin (head area).

Example 10

Transfection Studies with Expression Constructs and Antisense Constructs of HMGI-C and its Derivatives The above-mentioned cDNA fragment of the mouse or a corresponding antisense sequence was cloned into an eukaryotic expression vector. In this construct it is controlled by the LTR sequence of Moloney's virus of mouse sarcoma. The construct was then used for the lipofectin-mediated transfection in various primary and established cells. Stable transfectants were selected by means of ampicillin. It could be shown that upon transfection into primary human fetal fibroblasts the number of cumulative doublings of the transfectant population increased significantly over controls that were only transfected with the vector. A reverse effect was observed on transfection with the antisense construct. The same vector system was then used for cloning the described aberrant transcripts of the human HMGI-C; in this case as well, an increase in the number of cumulative doublings of the population was also obtained. Depending on the cDNA sequence used this increase was 10-35% higher than with the cDNA sequence of the mouse.

Example 11

DNA-Relaxant Effect of the Proteins Derived from the Aberrant Transcripts

Using the DNA sequences SEQ ID NOs: 1-19, consisting of parts of the cDNA sequence of the HMGI-C gene and other DNA sequences mostly appended to the $3^{rd}$ exon of this gene, recombinant proteins were synthesized in the expression vector pET7C and purified.

The proteins purified in this way were then tested for the formation of the so-called negative super coils, in the topoisomerase-mediated relaxation assay described by Nissen and Reeves (J. Biol. Chem. 270, 4355-4360, 1995). This investigations showed that the capacity to induce such negative super coils was in all derivatives higher than in the unmodified recombinant HMGI-C protein used as a control. The allowable conclusion that, among others, the interaction of the proteins with the DNA affects the therapeutic efficacy, leads to the deduction that all sequences shown possess an increased efficacy with regard to the applications mentioned.

Polypeptides Encoded by Polynucleotides Comprising the Sequences of SEQ ID NOs: 1-19 Promote DNA Bending Translation products that include polypeptide sequences encoded by SEQ ID NOs: 1-19 as well as the native HMGI genes/MAG gene possess a DNA relaxing or DNA bending activity which is exercised upon binding of the translation products to DNA sequences (see Example 11). Due to this change in the bending angle of the DNA in the promoter region of various genes a first access of a transcription complex or an access of a different transcription complex to the promotor region is possible, thus allowing for the modulation of expression of some distinct genes, as described below. Notably, the gene products of both the native sequences of HMGI genes/MAG genes, as well as the translation products of the aberrant transcripts according to SEQ ID NOs: 1-19 include at least exons 1-3, wherein each of the exons encodes a DNA binding domain. Each of said domains is able to bind to an AT "hook" (an AT-rich DNA sequence) which is present in the promotor region of the gene to be activated. Typically, it is sufficient that two of the domains bind to said AT hooks and this interaction provides for the bending of the DNA structure in the promotor region with the above-specified consequences of facilitating the formation of a transcription complex.

Polypeptides Including Sequences Encoded by the HMGI Genes/MAG Genes and SEQ ID NOs: 1-19 Affect the Regulation of Genes that Influence Development of Mesenchymal Tissues The above-specified characteristics of the HMGI genes/MAG genes and SEQ ID NOs: 1-19, namely to exhibit three AT hook binding domains, makes the gene products of the aforementioned nucleic acid sequences suitable for modulating the expression of genes that possess AT-rich DNA sequences (AT hooks), preferably in a promotor region.

Furthermore it is now know that the DNA relaxing/bending activity of translation products of HMGI genes/MAG genes/SEQ ID NOs: 1-19 acts on proliferatively active genes in the embryogenic phase (see Examples 8, 1), particularly genes for the development of mesenchymal tissues.

Products of the HMGI Genes/MAG Genes and SEQ ID NOs: 1-19 are Useful for Treating Tumors, Promoting Angiogenesis Treating Endometriosis, Stimulating Tissue Development and Contraception (1) Treatment of Tumors (a) Benign Tumors It has now been discovered that a mutation in the HMGI gene, or in close proximity thereto, is sufficient to induce a benign tumor (see Example 2). More particularly, it has been found that in benign tumors the chromosomal breakpoints can be both within the sequence of the HMGI genes/MAG genes or outside thereof. In the first case the conclusion can be drawn that translation products of aberrant transcripts, such as those disclosed in SEQ ID NOs: 1-19, are responsible for the observed tumors (see Example 2). In the second case, i.e., the chromosomal breakpoint is outside said genes, it is suggested that even wild type translation products, i.e., native HMGI genes/MAG genes, can also be responsible for the observed tumor. In the latter case it is noteworthy that changes in both the upstream and more particularly in the downstream environment of the native nucleic acid sequences are responsible for the observed HMGI genes/MAG gene expression which cannot be observed under normal conditions in tumor-free tissue.

(b) Malignant Tumors

It has been discovered that increased levels of translation products encoded by HMGI genes/MAG genes and SEQ ID NOs: 1-19 correlate with unfavorable tumor prognosis. Accordingly, detecting increased levels of these translation products compared with non-tumor or tumor tissue, is useful for determining the prognosis of a tumor. The tumor prognosis correlated inversely with the levels of these translation products.

The conclusion that gene products, or more particularly translation products of HMGI genes/MAG genes/SEQ ID NOs: 1-19, are useful for tumor therapy was based on the finding that tumor progression and expression of HMGI genes/MAG genes/SEQ ID NOs: 1-19 correlated with an unfavorable prognosis of the tumor. Accordingly, inhibiting tumor progression by reducing transcriptional activity of the HMGI genes/MAG genes/SEQ ID NOs: 1-19 would inhibit tumor progression, thereby leading to improved prognosis of malignant tumors.

(2) Angiogenesis

It was unexpectedly discovered that benign tumors contain blood vessels derived from the tumor itself (see Example 5) whereas blood vessels normally grow from the outside of the tumor into the same. Under the influence of HMGI/MAG gene translation products, and those of SEQ ID NOs: 1-19, new vessels can be generated within the tumor itself. Accordingly, HMGI genes/MAG genes/SEQ ID NOs: 1-19, and particularly their translation products are suitable for promoting angiogenesis in vivo.

(3) Endometriosis

It was discovered that endometriosis afflicted tissue in which HMGI, particularly HMGI-Y, was expressed (see Example 6). This was in contrast to the normal expression pattern of the lining of the corpus uteri. Based on this finding, it was considered that endometriosis might be a condition similar to the condition of endometrial polyps and to tumors observed in other tissues and organs with regard to the fact that HMGI-expression was increased. Tissue afflicted in the case of endometriosis was characterized in that both mesenchymal and epithelial tissues showed increased proliferation. Accordingly, treatments that reduced expression of HMGI genes/MAG genes/SEQ ID NOs: 1-19, more preferably HMGI-Y expression, in the lining of the corpus uteri would improve symptoms associated with endometriosis.

(4) Tissue Regeneration

While studying the expression of HMGI genes/MAG genes and polynucleotides having the sequences of SEQ ID NOs: 1-19 in benign tumors it was discovered that tissue could regenerate under the influence of the HMGI mutations, which lead either to the formation of wild type translation products of the HMGI/MAG genes or aberrant proteins (such as those encoded by SEQ ID NOs: 1-19) (see Examples 4, 9). Tissue regenerated under these conditions was identical to the tissue from which the tumor originated. This was observed for fatty or adipose tissue, cartilage, more particularly hyaline cartilage and smooth muscle. In all of these cases the regenerated tissue exhibited all the characteristics of the differentiated tissue from which it originated and was thus not dedifferentiated, as would have been expected based on knowledge about other tumors that typically exhibit tumor-derived cells showing distinct dedifferentiation.

Regenerated fatty tissue may be used in applications that include plastic surgery. Regeneration of cartilage will be useful for repair of both traumatic injury and degenerative changes, including sports damages and arthrosis.

(5) Contraception

It now has been discovered that formation of the placenta requires activity of the HMGI genes (see Example 7). It has further been shown that if HMGI-C is inactive this lack can be compensated by expression of HMGI-Y. Accordingly, it is thus concluded that contraception can be performed by blocking translation and/or transcription of the HMGI/MAG genes.

Methods Based on Modulating the Expression of HMGI Genes/MAG Genes and Derivatives Thereof Methods useful in connection with: (1) the treatment of tumors; (2) treatment of endometriosis; and (3) contraception, involve blocking or inhibiting the activity of the translation products of the HMGI genes/MAG genes and their derivatives, including SEQ ID NOs: 1-19. This can be accomplished by inhibiting mRNA translation or transcriptional activation using antisense nucleic acids. Alternatively, ribozymes targeted to the mRNAs encoding these proteins can be made and used to inactivate the mRNAs. Still another method of blocking or inhibiting the activity of the translation products of the HMGI genes/MAG genes and their derivatives, including SEQ ID NOs: 1-19 includes producing high intracellular levels of translation products or mimics thereof. More specifically, high intracellular levels of translation products of the HMGI genes/MAG genes or the sequences of SEQ ID NOs: 1-19 can be used for competitive binding to target sequences so that the promotor normally activated by the translation products of the HMGI genes/MAG genes/SEQ ID NOs: 1-19 can no longer be activated ("flooding" of the cell). Molecules which mimic targets of the translation products of the HMGI genes/MAG genes/SEQ ID NOs: 1-19 can compete with their natural targets, thereby resulting in inhibition of the intracellularly present translation products of the HMGI genes/MAG genes/SEQ ID NOs: 1-19. Such molecules can be selected from the group that includes nucleic acid sequences comprising at least one AT hook or at least one AT hook-like structure, and molecules exhibiting the structure and/or binding characteristics of AT hooks. Preferably, the molecule is a nucleic acid molecule, however, it is not restricted to polynucleotides.

Methods useful for promoting tissue regeneration involve stimulating the expression of HMGI genes/MAG genes or their derivatives, including SEQ ID NOs: 1-19. For example, this activation can be accomplished by administering cells in vitro or in vivo a chemical compound. Such a compound may act either specifically or non-specifically. Activation of HMGI genes/MAG genes/SEQ ID NOs: 1-19 can be promoted, for example, by contacting cells with different compounds, including phorbol esters. Is also is possible to activate genes responsible for further growth of differentiated tissue by introducing HMGI genes/MAG genes including SEQ ID NOs: 1-19 into the respective cells and tissue by means of gene therapy. For this purpose the respective nucleic acid sequences, particularly according to SEQ ID NOs: 1-19, are put under control of a strong promotor, which optionally can be activated and deactivated upon administration of a stimulus to the cell/tissue. Yet another approach for promoting tissue regeneration involves administering directly to the respective cell/tissue a translation product, either a peptide or a protein, that is derived from HMGI genes/MAG genes or SEQ ID NOs: 1-19. Due to the low molecular weight of any of the aforementioned translation products these peptides/proteins can easily be applied to the cell, for example using encapsulation delivery systems.

Methods useful for treating angiogenesis vary according to whether it is intended to increase or decrease angiogenesis in a particular situation. In the case where growth of vessels is to be promoted, such as in case of improving vessel supply of infarct-damaged myocardial tissue, an increased expression of HMGI genes/MAG genes including SEQ ID NOs: 1-19 is to be realized which can be performed according to the measures as outlined above. However, if angiogenesis is to be inhibited, such as might be the case in the treatment of tumor diseases or diseases of the eye resulting from neovascularization, expression of the HMGI genes/MAG genes, including SEQ ID NOs: 1-19, is to be suppressed according to one of the above-specified approaches.

The features of the invention revealed in the preceding description and in the claims can, both alone and in any combination, be of significance for the realization of the invention in its various forms of implementation.

What is claimed is:

1. A method for proliferating cartilage cells comprising administering to said cartilage cell an HMGA2 protein of SEQ ID NO:14.

* * * * *

SEQUENCE LISTING

<160> NUMBER OF SEQ ID NOS: 23

<210> SEQ ID NO 1
<211> LENGTH: 566
<212> TYPE: DNA
<213> ORGANISM: Homo sapiens

<400> SEQUENCE: 1

```
atgagcgcac gcggtgaggg cgcggggcag ccgtccactt cagcccaggg acaacctgcc      60
gccccagcgc ctcagaagag aggacgcggc cgccccagga agcagcagca agaaccaacc     120
ggtgagccct ctcctaagag acccagggga agacccaaag gcagcaaaaa caagagtccc     180
tctaaagcag ctcaaaagaa agcagaagcc actggagaaa aacggccaag aggcagacct     240
aggaaatgga ataaacagga ttcccaggag tgacttggtt ctgaatgact tggaagtcaa     300
aaggaagagt ccgtttctcc agtaacaaaa gtctgcctga caagaggctc taagctgtcc     360
tggatgccaa tctttgtgcc gactacttta cagtgattga ttgctcatac ttcacggcaa     420
ccctgtggaa tagataacat catcatcccc cttttttactg aggtgtgggg aagttacctc     480
tattgcccat gatcatagtt tagctggcgc tgctttataa aagaatgaat gaataaatta     540
atgaatgaaa aaaaaaaaaa aaaaaa                                         566
```

<210> SEQ ID NO 2
<211> LENGTH: 615
<212> TYPE: DNA
<213> ORGANISM: Homo sapiens

<400> SEQUENCE: 2

```
atgagcgcac gcggtgaggg cgcggggcag ccgtccactt cagcccaggg acaacctgcc      60
gccccagcgc ctcagaagag aggacgcggc cgccccagga agcagcagca agaaccaacc     120
ggtgagccct ctcctaagag acccaggggw agacccaaag gcagcaaaaa caagagtccc     180
tctaaagcag ctcaaaagaa agcagaagcc actggagaaa aacggccaag aggcagacct     240
```

```
aggaaatggw ataaacagga ttcccaggag tgacttggyt ctgaatgact tggaagtcaa    300
aaggaagagt ccgyytctcc agtaacaaaa gtatgcctga caagaggctc taagctgtcc    360
tggatgccaa tctttgtgcc gactacttta cagtgattga ttgctcatac ctcacggsaa    420
ccctgtggta tagataacat catcatcccc ccttttactg aggtgtgggg aagtttatct    480
ctattgccca tgatcatagt ttagctggcg ctgctttata aagaatgwa tgwagaaatt    540 aatgwatgaa aaaaaaaaaa aaaaaaaaaa aaaaaaaaaa aaaaaaaaaa aaaaaaaga    600 tgtcgacgga tcctt                                                    615

<210> SEQ ID NO 3
<211> LENGTH: 849
<212> TYPE: DNA
<213> ORGANISM: Homo sapiens

<400> SEQUENCE: 3
atgagcgcac gcggtgaggg cgcggggcag ccgtccactt cagcccaggg acaacctgcc     60
gccccagcgc ctcagaagag aggacgcggc cgccccagga agcagcagca agaaccaacc    120
ggtgagccct ctcctaagag acccagggga ggacccaaag gcagcaaaaa caagagtccc    180
tctaaagcag ctcaaaagaa agcagaagcc actggagaaa aacggccaag aggcagacct    240
aggaaatgga agaagacagg aatgtcaggc ctctgagctc aagctaagcc atcatatccc    300
ctgtgacctg yatgtataca tccagatggc ctgaagcaac tgaagcatcc acaaaagaag    360
tgcaaatagc caggtcctgc cttagsttga cgacattcca ccattgtgac ctgttcctgc    420
cgcaccctaa ctgatcaatt gaccttatga caatacaccc tccccgccct tgagataatg    480
tactttgaga tatyccccct acccttgaga aggtactttg tgatatttcc ccaccccttga    540 gaaggtactt tgtgatattc tcccacccct tgagaagttac tttgtgatat tcccccaccc    600
ttgagaaggt actttgtgat attccccac ccttgaaaag gtactttgta atactctccc    660
tgcccttgag aatgtacttt gtgagatcta ccccctgctc ctaactcaac cgcctatccc    720
aaacctataa gaactaacga taatcccacc acactttgct cactctcttt tcagactcag    780
cccacctgca cccaggtgat taaaaagctt tattgctcac acaaaaaaaa aaaagatgtc    840
gacggatcc                                                            849

<210> SEQ ID NO 4
<211> LENGTH: 774
<212> TYPE: DNA
<213> ORGANISM: Homo sapiens

<400> SEQUENCE: 4
atgagcgcac gcggtgaggg cgcggggcag ccgtccactt cagcccaggg acaacctgcc     60
gccccagcgc ctcagaagag aggacgcggc cgccccagga agcagcagca agaaccaacc    120
ggtgagccct ctcctaagag actcagggga agacccaaag gcagcaaaaa caagagtccc    180
tctaaagcag ctcaaaagaa agcagaagcc actggagaaa aacggccaag aggcagacct    240
aggaaatggc cacaacaagt tgttcagaag aagcctgctc aggttcatgc tggaggatga    300
accattgcca gcagccggaa cgactgccag cgactcctgc ttcctttgct ctaccttctc    360
taccctatcc ttaatattat tacaggagca agcctccatt gactttctgt tcctaaaaca    420
ggcatgacgc tactattttc cctttccaca gataatactt caaaaagagt tcgtaagtta    480
cccaatgcca aatatataaa attggcatat taattgcact gcatctacta cgtgtagcta    540
```

-continued

```
agattcaaat ttctcagcaa ggtcttcatt atccagccta acctaactt   caccaatctc      600 ctcaaaattt gtattccagc cttgatgaat ttatcttcct gcaataaaga atatttgctg      660
tcaaaaaaaa aaaaaaaaag atgtcgacgg atcctttagt agtagtaggc ggccgctcta      720
gaggatccaa gcttacgtac gcgtgcatgc gacgtcatag ctcttctata gtgt            774
```

<210> SEQ ID NO 5
<211> LENGTH: 506
<212> TYPE: DNA
<213> ORGANISM: Homo sapiens

<400> SEQUENCE: 5

```
atgagcgcac gcggtgaggg cgcggggcag ccgtccactt cagcccaggg acaacctgcc       60
gccccagcgc ctcagaagag aggacgcggc cgccccagga agcagcagca agaaccaacc      120
ggtattaaga agagagaaag aatctgagaa attatggcgt actcaactgt ggacagctga      180
aagtctggca tagcgtgccc tcatcatcac aaatgggctc gcattacaag ctacacttat      240
ttgacaacta tcagcatttg tcaaccggca ctcagatttg aagactcatt tcacagctgg      300
agcaagagaa gacaggaagg aaaaatcaga gtaaggtttc aatgagtttc tgcaaattct      360
cagaagtttt gctgccactc agtgtcacaa taacaaaaag aaataaaaat agctgatatt      420
tactaaacaa aaaaaaaaaa gatgtcgacg gatcctttag tagtagtagg cggccgctct      480
agaggatcca agcttacgta cgcgtg                                           506
```

<210> SEQ ID NO 6
<211> LENGTH: 349
<212> TYPE: DNA
<213> ORGANISM: Homo sapiens

<400> SEQUENCE: 6

```
atgagcgcac gcggtgaggg cgcggggcag ccgtccactt cagcccaggg acaacctgcc       60
gccccagcgc ctcagaagag aggacgcggc cgccccagga agcagcagca agaaccaacc      120
ggtgagccct ctcctaagag acccagggga agacccaaag gcagcaaaaa caagagtccc      180
tctaaagcag ctcaaaagaa agcagaagcc actggagaaa aacggccaag aggcagacct      240
aggaaatggc ctactattgc actttgcaca cactggataa acatctgctg aatgagtgga      300
caataaaaca gaagcawatt tgttctaaaa aaaaaaaaa  aaaaaaaa                   349
```

<210> SEQ ID NO 7
<211> LENGTH: 739
<212> TYPE: DNA
<213> ORGANISM: Homo sapiens

<400> SEQUENCE: 7

```
atgagcgcac gcggtgaggg cgcggggcag ccgtccactt cagcccaggg acaacctgcc       60
gccccagcgc ctcagaagag aggacgcggc cgccccagga agcagcagca agaaccaacc      120
ggtgagccct ctcctaagag acccagggga agacccaaag gcagcaaaaa caagagtccc      180
tctaaagcag ctcaaaggaa agcagaagcc actggagaaa aacggccaag aggcagacct      240
aggaaatggg acaatctact accaagaacc agctccaaga agaaaacatc tctgggaaac      300
agtaccaaaa ggagtcactg aattgtcatt ggaggagtcc aggatagctc ttcatgttat      360
tttcaccttg aggaattgtc cattacatct atgagcctta tgtgtggctt tctccgatat      420
agaaacctat caggtgtctt ttagatcatt ttcaaaacac tggctttatt ctttcttatg      480
tttccaacct gaagtctgca tcccaagatg tagtttcact gctaccccat atggcaccct      540
```

```
cgtacgaatt tgaaaaaagt actcactcta ggcacatgca gagccatgcc tgcggggaca    600
gcttagagag tagagggtgg gctgaactcc agttactctc gtacagggat ccaccttttt    660
gcagaaatca cagtgtggct atggtgtggt ttgatttcat aaaacagatg cttaaaaaag    720
taaaaaaaaa aaaaaaaaa                                                 739

<210> SEQ ID NO 8
<211> LENGTH: 533
<212> TYPE: DNA
<213> ORGANISM: Homo sapiens

<400> SEQUENCE: 8
atgagcgcac gcggtgaggg cgcggggcag ccgtccactt cagcccaggg acaacctgcc     60
gccccagcgc tcagaagag aggacgcggc cgccccagga agcagcagca agaaccaacc    120
ggtgagccct ctcctaagag acccagggga agacccaaag gcagcaaaaa caagagtccc    180
tctaaagcag ctcaaaagaa agcagaagcc actggagaaa aacggccaag aggcagacct    240
aggaaatggg tggacaggaa gtagaattta ttgctgtagt aatggcttct ggagaaatgg    300
cagaaatcaa tgagaattag ccaaaccaat tccatgaaca attccggtaa gtcatgtcct    360
ctccatttct gcaagtcagg attaggctgc ttcagctcac actccagtgc tccaacaaat    420
agagaaaaga aacattcctc atgcctcttg aactgccctg ctgtaaaatc catatgttga    480
aaacatctta aggcactcca ataaacaatc ttctttttgc aaaaaaaaaa aaa           533

<210> SEQ ID NO 9
<211> LENGTH: 358
<212> TYPE: DNA
<213> ORGANISM: Homo sapiens

<400> SEQUENCE: 9
atgagcgcac gcggtgaggg cgcggggcag ccgtccactt cagcccaggg acaacctgcc     60
gccccagcgc tcagaagag aggacgcggc cgccccagga agcagcagca agaaccaacc    120
ggtgagccct ctcctaagag cacccagggg caaggcccaa wggcagcaaa acaagagtc    180 cctctaaagc agctcaaaag aaagcagaag ccactggaga aaacggcca agaggcagac    240 ctaggaaatg gcctactatt gcactttgca cacactggat aaacatctgc tgaatgagtg    300
gacaataaaa cagaagcaaa tttgttctaa aaaaaaaaaa aaaaaagcwt gtcgacgg     358

<210> SEQ ID NO 10
<211> LENGTH: 850
<212> TYPE: DNA
<213> ORGANISM: Homo sapiens

<400> SEQUENCE: 10
atgagcgcac gcggtgaggg cgcggggcag ccgtccactt cagcccaggg acaacctgcc     60
gccccagcgc tcagaagag aggacgcggc cgccccagga agcagcagca agaaccaacc    120
ggtgagccct ctcctaagag acccagggga ggacccaaag gcagcaaaaa caagagtccc    180
tctaaagcag ctcaaaagaa agcagaagcc actggagaaa aacggccaag aggcagacct    240
aggaaatgga agaagacagg aatgtcaggc ctctgagctc aagctaagcc atcatatccc    300
ctgtgacctg yatgtataca tccagatggc ctgaagcaac tgaagcatcc acaaaagaag    360
tgcaaatagc caggtcctgc cttagsttga cgacattcca ccattgtgac ctgttcctgc    420
cgcaccctaa ctgatcaatt gaccttatga caatacaccc tccccgccct tgagataatg    480
```

```
tactttgaga tatyccccct acccttgaga aggtactttg tgatatttcc ccacccttga    540
gaaggtactt tgtgatattc tcccaccctt gagaagttac tttgtgatat tcccccaccc    600
ttgagaaggt actttgtgat attccccac ccttgaaaag gtactttgta atactctccc     660
tgcccttgag aatgtacttt gtgagatcta cccctgctc ctaactcaac cgcctatccc     720
aaacctataa gaactaacga taatcccacc acactttgct cactctcttt tcagactcag    780
cccacctgca cccaggtgat taaaaagctt tattgctcac acaaaaaaaa aaagatgtc     840 gacggatcct                                                           850
```

<210> SEQ ID NO 11
<211> LENGTH: 533
<212> TYPE: DNA
<213> ORGANISM: Homo sapiens

<400> SEQUENCE: 11

```
atgagcgcac gcggtgaggg cgcggggcag ccgtccactt cagcccaggg acaacctgcc     60
gccccagcgc ctcagaagag aggacgcgac cgccccagga agcagcagca agaaccaacc    120
ggtgagccct ctcctaagag acccagggga agacccaaag gcagcaaaaa caagagtccc    180
tctaaagcag ctcaaaagaa agcaggagcc actggagaaa aacggccaag aggcagacct    240
aggaaatggg ttaagaaatt gtcactgcca ccccaacctt cagcaaaaac caccctgatc    300
aatccgcagc catcaacact gaggcaagac cctccttcac cagcaaaagg attacgactc    360
actgaaggtt cagatgatca ttagcatttt ctagcaataa agtattttta attaaggtaa    420
aaaaaaaaaa aaaagatgt cgacggatcc tttagtagta ggcggccgct ctagaggatc    480
caagcttacg tacgcgtgca tgcgacgtca tagctcttct atagtgtcac cta          533
```

<210> SEQ ID NO 12
<211> LENGTH: 528
<212> TYPE: DNA
<213> ORGANISM: Homo sapiens
<220> FEATURE:
<221> NAME/KEY: misc_feature
<222> LOCATION: (1)...(528)
<223> OTHER INFORMATION: n = A, T, C or G

<400> SEQUENCE: 12

```
atgagcgcac gcggtgaggg cgcggggcag ccgtccactt cagcccaggg acaacctgcc     60
gccccagcgc ctcagaagag aggacgcggc cgccccagga agcagcagca agaaccaacc    120
ggtgagccct ctcctaagag acccagggga agacccaaag gcagcaaaaa caggagtccc    180
tctaaagcag ctcaaaagaa agcagaagcc actggagaaa aacggccaag aggcagacct    240
aggaaatgga atacaaaaa tacatctcaa aattcgtaaa aaatctgaaa ggaccctcta    300
tggccaaaat aatcttgaag aagatgaaaa agttgaaga atgcacactt cctaatttct     360
acttaccagt attctacagt aatcattgtg gaactattaa tagcatacag acatattaga    420
ctaacagaat ggaatagagg gccccaaaat aaatgccagc atatatggnc aaacgaaaaa    480
aaaaaaaaaa aaaaaaaaaa aaaaaaaaa agatgtcgac ggatcctt               528
```

<210> SEQ ID NO 13
<211> LENGTH: 495
<212> TYPE: DNA
<213> ORGANISM: Homo sapiens

<400> SEQUENCE: 13

```
atgagcgcac gcggtgaggg cgcggggcag ccgtccactt cagcccaggg acaacctgcc     60
```

| | |
|---|---|
| gccccagcgc ctcagaagag aggacgcggc cgccccagga agcagcagca agaaccaacc | 120 |
| ggtgagccct ctcctaagag acccagggga agacccaaag gcagcaaaaa caagagtccc | 180 |
| tctaaagcag ctcaaaagaa agcagaagcc actggagaaa aacggccaag aggcagacct | 240 |
| aggaaatggc cacaacaagt tgttcagaag aagcctgctc aggtcaatgt tgccttgcct | 300 |
| gggaaggacc acccgggcaa tcttatatat ctactgytct ctaaaaatgc cacttagaag | 360 |
| agaattgaaa cttccaaaca catgaaagga tccaaggaaa gtgtcttcaa acaattacat | 420 |
| atgagcttta gtggaataa aaacagagtt accatgaaaa aaaaaaaaa aaaaaaaag | 480 |
| attcgacgga tcctt | 495 |

<210> SEQ ID NO 14
<211> LENGTH: 689
<212> TYPE: DNA
<213> ORGANISM: Homo sapiens

<400> SEQUENCE: 14

| | |
|---|---|
| atgagcgcac gcggtgaggg cgcggggcag ccgtccactt cagcccaggg acaacctgcc | 60 |
| gccccagcgc ctaagaagag aggacgcggc cgccccagga agcagcagca agaaccaacc | 120 |
| ggtgagccct ctcctaagag acccagggga agacccaaag gcagcaaaaa caagagtccc | 180 |
| tctaaagcag ctcaaaagaa agcagaagcc actggagaaa aacggccaag aggcagacct | 240 |
| aggaaatggc cacaacaagt tgttcagaag aagcctgctc aggaggaaac tgaagagaca | 300 |
| tcctcacaag agtctgccga agaagactag ggggcgccaa cgttcgattt ctacctcagc | 360 |
| aggagttggy atcttttgaa gggagaagac actgcagtga ccacttattc tgggctcttt | 420 |
| ctccacaccc accctcaagg ctacctctat ctccacctag cctcttaata tctccaccaa | 480 |
| agagcaaatc agttgactga agtcccagct actcaggaga ctgaagcagg agaatcactt | 540 |
| gaacctggga ggcggaggtt gcagtgagcc gagatcacgc caccgcactc cagcctgggc | 600 |
| aacagagcga gactccatct aacaataata caataaagc tattgrccaa aaaaaaaaa | 660 |
| aaaaaaaaaa aagatgtcga cggatcctt | 689 |

<210> SEQ ID NO 15
<211> LENGTH: 442
<212> TYPE: DNA
<213> ORGANISM: Homo sapiens

<400> SEQUENCE: 15

| | |
|---|---|
| atgagcgcac gcggtgaggg cgcggggcag ccgtccactt cagcccaggg acaacctgcc | 60 |
| gccccagcgc ctcagaagag aggacgcggc cgccccagga agcagcagca agaaccaacc | 120 |
| ggtgagccct ctcctaagag acccagggga agacccaaag gcagcaaaaa caagagtccc | 180 |
| tctaaagcgg ctcaaaagaa agcagaagcc actggagaaa aacggccaag aggcagacct | 240 |
| aggaaatggc cacaacaagt tgttcagaag aagcctgctc aggactgact caagatactc | 300 |
| atgaacgtgg aaaactccta aatgtgtcat tctgagttcc tgagaagttg aacatacaca | 360 |
| gatgacaaag aagaatgcca tttagccata actacccttt ctagattacc aagtatttgt | 420 |
| aggtttattg gcaagatagc tt | 442 |

<210> SEQ ID NO 16
<211> LENGTH: 452
<212> TYPE: DNA
<213> ORGANISM: Homo sapiens

<400> SEQUENCE: 16

```
atgagcgcac gcggtgaggg cgcggggcag ccgtccactt cagcccaggg acaacctgcc    60
gccccagcgc ctcagaagag aggacgcggc cgccccagga agcagcagca agaaccaacc   120
ggtgagccct ctcctaagag acccagggga agacccaaag gcagcaaaaa caagagtccc   180
tctaaagcag ctcaaaagaa agcagaagcc actggagaaa aacggccaag aggcagacct   240
aggaaatgga ataaacagga ttcccaggag tgacttggtt ctgaatgact tggaagtcaa   300
aaggaagagt ccgtttctcc agtaacaaaa gtatgcctga caagaggctc taagctgtcc   360
tggatgccaa tctttgtgcc gtwctacttt acaggtgatt gattgctcat acttcacggc   420
aaccctgtgg aatagataac atcatcatcc cc                                  452
```

<210> SEQ ID NO 17
<211> LENGTH: 430
<212> TYPE: DNA
<213> ORGANISM: Homo sapiens

<400> SEQUENCE: 17

```
atgagcgcac gcggtgaggg cgcggggcag ccgtccactt cagcccaggg acaacctgcc    60
gccccagcgc ctcagaagag aggacgcggc cgccccagga agcagcagca agaaccaacc   120
ggtgagccct ctcctaagag acccagggga agacccaaag gcagcaaaaa caagagtccc   180
tctaaagcag ctcaaaagaa agcagaagcc actggagaaa aacggccaag aggcagacct   240
aggaaatggg aggagtttta cattgcagct tagaagcctt tcttccaata gcagagattt   300
ggtgtcatgt ggtgttcatc agtttgaaaa gaagtatttc tgctgtttgc ctcaagatgt   360
acatacagag atgtgctgat tctcagaact tctatagaat tccattagcc agtcctgcca   420
attgaaattt                                                            430
```

<210> SEQ ID NO 18
<211> LENGTH: 456
<212> TYPE: DNA
<213> ORGANISM: Homo sapiens

<400> SEQUENCE: 18

```
atgagcgcac gcggtgaggg cgcggggcag ccgtccactt cagcccaggg acaacctgcc    60
gccccagcgc ctcagaagag aggacgcggc cgccccagga agcaggagca agaaccaacc   120
ggtgagccct ctcctaagag acccagggga gtacccaaag gcagcaaaaa caagagtccc   180
tctaaagcag ctcaaaagaa agcagaagcc actggagaaa aacggccaag aggcagacct   240
aggaaatgga agaagacagg aatgtcaggc ctctgagctc aagctaagcc atcatatccc   300
ctgtgacctg catgtataca tccagatggc ctgaagcaac tgaagatcca caaagaagt   360
gcaaatagcc aggtcctgcc ttagctgacg acattccacc attgtgacct gttcctgccg   420
caccctaact gatcaattga ccttatgaca atacac                              456
```

<210> SEQ ID NO 19
<211> LENGTH: 797
<212> TYPE: DNA
<213> ORGANISM: Homo sapiens

<400> SEQUENCE: 19

```
atgagcgcac gcggtgaggg cgcggggcag ccgtccactt cagcccaggg acaacctgcc    60
gccccagcgc ctcagaagag aggacgcggc cgccccagga agcagcagca agaaccaacc   120
ggtgagccct ctcctaagag acccagggga agacccaaag gcagcaaaaa caagagtccc   180
```

-continued

```
tctaaagcag ctcaaaagaa agcagaagcc actggagaaa aacggccaag aggcagacct      240
aggaaatggg tcacagtcaa agtgcctcag aagaactcat aagaatcatg caagcttcct      300
ccctcagcca ttgatggaaa gttcagcaag atcagcaaca aaaccaagaa aaatgatcct      360
tgcgtgctga atatctgaaa agagaaattt ttcctacaaa atctcttggg tcaagaaagt      420
tctagaattt gaattgataa acatggtggg ttggytgagg gtaagagtat atgaggaacc      480
ttttaaacga caacaatact gctagctttc aggatgattt ttraaaaata gattcaaatg      540
tgttatcctc tctctgaaac gcttcctata actcgagttt ataggggaag aaaaatctat      600
tgtttacaat tatatcacca ttaaggcaac tgctacaccc tgctttgtat tctgggctaa      660
gattcattra aarctagctg ctcttaaaaa aaaaaaaaaa aaaaaagatg tcgacggatc      720
ctttagtagt agtaggcggc cgctctagag gatccaagct tacgtacgcg tgcatgcgac      780
gtcatagctc gtctata                                                    797
```

```
<210> SEQ ID NO 20
<211> LENGTH: 18
<212> TYPE: DNA
<213> ORGANISM: Artificial Sequence
<220> FEATURE:
<223> OTHER INFORMATION: Primer

<400> SEQUENCE: 20
cttcagccca gggacaac                                                    18

<210> SEQ ID NO 21
<211> LENGTH: 18
<212> TYPE: DNA
<213> ORGANISM: Artificial Sequence
<220> FEATURE:
<223> OTHER INFORMATION: Primer

<400> SEQUENCE: 21
cgcctcagaa gagaggac                                                    18

<210> SEQ ID NO 22
<211> LENGTH: 18
<212> TYPE: DNA
<213> ORGANISM: Artificial Sequence
<220> FEATURE:
<223> OTHER INFORMATION: Primer

<400> SEQUENCE: 22
ttcctaggcc tgcctctt                                                    18

<210> SEQ ID NO 23
<211> LENGTH: 18
<212> TYPE: DNA
<213> ORGANISM: Artificial Sequence
<220> FEATURE:
<223> OTHER INFORMATION: Primer

<400> SEQUENCE: 23
tcctcctgag caggcttc                                                    18
```